United States Patent
Levy et al.

(10) Patent No.: US 8,926,681 B2
(45) Date of Patent: Jan. 6, 2015

(54) VASCULAR REMODELING DEVICE

(75) Inventors: Elad Israel Levy, Amherst, NY (US); Victoria Schuman, Long Beach, CA (US); Sanjay Shrivastava, Irvine, CA (US); Earl Slee, Laguna Niguel, CA (US)

(73) Assignee: Covidien LP, Mansfield, MA (US)

( * ) Notice: Subject to any disclaimer, the term of this patent is extended or adjusted under 35 U.S.C. 154(b) by 905 days.

(21) Appl. No.: 13/016,858

(22) Filed: Jan. 28, 2011

(65) Prior Publication Data
US 2011/0184453 A1 Jul. 28, 2011

Related U.S. Application Data

(60) Provisional application No. 61/299,266, filed on Jan. 28, 2010.

(51) Int. Cl.
| | | |
|---|---|---|
| *A61F 2/06* | (2013.01) | |
| *A61M 29/00* | (2006.01) | |
| *A61L 31/14* | (2006.01) | |
| *A61L 31/06* | (2006.01) | |
| *A61L 31/04* | (2006.01) | |
| *A61F 2/07* | (2013.01) | |
| *A61B 17/12* | (2006.01) | |

(52) U.S. Cl.
CPC .............. *A61B 17/12022* (2013.01); *A61F 2/07* (2013.01); *A61B 2017/12054* (2013.01); *A61L 31/148* (2013.01); *A61B 17/12172* (2013.01); *A61B 17/12118* (2013.01); *A61L 31/06* (2013.01); *A61B 2017/12063* (2013.01); *A61L 31/041* (2013.01); *A61B 17/1214* (2013.01)
USPC ........................... 623/1.11; 606/191; 606/200

(58) Field of Classification Search
USPC ........ 623/1.11, 1.12; 606/157, 158, 191, 192, 606/198, 200
See application file for complete search history.

(56) References Cited

U.S. PATENT DOCUMENTS

| 4,425,908 A | 1/1984 | Simon |
|---|---|---|
| 4,619,246 A | 10/1986 | Molgaard-Nielsen et al. |

(Continued)

FOREIGN PATENT DOCUMENTS

| CN | 101472537 A | 7/2009 |
|---|---|---|
| DE | 102008028308 | 4/2009 |

(Continued)

OTHER PUBLICATIONS

International Search Report and Written Opinion dated May 5, 2011 in International Application No. PCT/US 11/23058.

(Continued)

*Primary Examiner* — Darwin Erezo
*Assistant Examiner* — Lindsey Bachman
(74) *Attorney, Agent, or Firm* — Mark J. Kertz, Esq.

(57) ABSTRACT

A generally spherical vascular remodeling device is permanently positionable at a junction of afferent and efferent vessels of a bifurcation having an aneurysm. After positioning the device at the junction to substantially conform the device to the shape of the junction, the device acts as a scaffolding to inhibit herniation of objects out of the aneurysm and permits perfusion to the efferent vessels. Positioning the device may include deployment and mechanical or electrolytic release from a catheter. Embolic material may be inserted in the aneurysm before or after positioning the device. The device may have a first end, a second end substantially opposite to the first end, and a plurality of polymer filaments extending between and coupled at the first end and the second end. Such devices may be football shaped, pumpkin shaped, or twisted. The device may include a plurality of polymer loops forming a generally spherical shape.

11 Claims, 25 Drawing Sheets

(56) References Cited

U.S. PATENT DOCUMENTS

| | | |
|---|---|---|
| 4,655,771 A | 4/1987 | Wallsten |
| 4,768,507 A | 9/1988 | Fischell et al. |
| 4,921,484 A | 5/1990 | Hillstead |
| 4,998,539 A | 3/1991 | Delsanti |
| 5,026,377 A | 6/1991 | Burton et al. |
| 5,061,275 A | 10/1991 | Wallsten et al. |
| 5,064,435 A | 11/1991 | Porter |
| 5,104,404 A | 4/1992 | Wolff |
| 5,122,136 A | 6/1992 | Guglielmi et al. |
| 5,222,971 A | 6/1993 | Willard et al. |
| 5,250,071 A | 10/1993 | Palermo |
| 5,334,210 A | 8/1994 | Gianturco |
| 5,378,239 A | 1/1995 | Termin et al. |
| 5,405,379 A | 4/1995 | Lane |
| 5,425,984 A | 6/1995 | Kennedy et al. |
| 5,484,444 A | 1/1996 | Braunschweiler et al. |
| 5,499,981 A | 3/1996 | Kordis |
| 5,527,338 A | 6/1996 | Purdy |
| 5,545,208 A | 8/1996 | Wolff et al. |
| 5,549,635 A | 8/1996 | Solar |
| 5,624,461 A | 4/1997 | Mariant |
| 5,634,942 A | 6/1997 | Chevillon et al. |
| 5,645,558 A | 7/1997 | Horton |
| 5,690,671 A | 11/1997 | McGurk et al. |
| 5,725,552 A | 3/1998 | Kotula et al. |
| 5,728,906 A | 3/1998 | Eguchi et al. |
| 5,733,294 A | 3/1998 | Forber et al. |
| 5,741,333 A | 4/1998 | Frid |
| 5,749,891 A | 5/1998 | Ken et al. |
| 5,749,919 A | 5/1998 | Blanc |
| 5,749,920 A | 5/1998 | Quiachon et al. |
| 5,766,151 A | 6/1998 | Valley et al. |
| 5,814,062 A | 9/1998 | Sepetka et al. |
| 5,830,230 A | 11/1998 | Berryman et al. |
| 5,846,261 A | 12/1998 | Kotula et al. |
| 5,879,366 A | 3/1999 | Shaw et al. |
| 5,911,731 A | 6/1999 | Pham et al. |
| 5,916,235 A | 6/1999 | Guglielmi |
| 5,925,060 A | 7/1999 | Forber |
| 5,928,228 A | 7/1999 | Kordis et al. |
| 5,928,260 A | 7/1999 | Chin et al. |
| 5,935,148 A | 8/1999 | Villar et al. |
| 5,935,362 A | 8/1999 | Petrick |
| 5,941,249 A | 8/1999 | Maynard |
| 5,944,738 A | 8/1999 | Amplatz et al. |
| 5,951,599 A | 9/1999 | McCrory |
| 5,957,948 A | 9/1999 | Mariant |
| 5,980,554 A | 11/1999 | Lenker et al. |
| 6,010,517 A | 1/2000 | Baccaro |
| 6,024,756 A | 2/2000 | Huebsch et al. |
| 6,033,423 A | 3/2000 | Ken et al. |
| 6,036,720 A | 3/2000 | Abrams et al. |
| 6,063,070 A | 5/2000 | Eder |
| 6,063,104 A | 5/2000 | Villar et al. |
| 6,086,577 A | 7/2000 | Ken et al. |
| 6,093,199 A | 7/2000 | Brown et al. |
| 6,096,034 A | 8/2000 | Kupiecki et al. |
| 6,096,073 A | 8/2000 | Webster et al. |
| 6,099,526 A | 8/2000 | Whayne et al. |
| 6,123,715 A | 9/2000 | Amplatz |
| 6,139,564 A | 10/2000 | Teoh |
| 6,152,144 A | 11/2000 | Lesh et al. |
| 6,168,592 B1 | 1/2001 | Kupiecki et al. |
| 6,168,615 B1 | 1/2001 | Ken et al. |
| 6,168,618 B1 | 1/2001 | Frantzen |
| 6,168,622 B1 | 1/2001 | Mazzocchi |
| 6,183,495 B1 | 2/2001 | Lenker et al. |
| 6,190,402 B1 | 2/2001 | Horton et al. |
| 6,193,708 B1 | 2/2001 | Ken et al. |
| 6,221,086 B1 | 4/2001 | Forber |
| 6,261,305 B1 | 7/2001 | Marotta et al. |
| 6,306,141 B1 | 10/2001 | Jervis |
| 6,309,367 B1 | 10/2001 | Boock |
| 6,322,576 B1 | 11/2001 | Wallace et al. |
| 6,325,820 B1 | 12/2001 | Khosravi et al. |
| 6,331,184 B1 | 12/2001 | Abrams |
| 6,332,576 B1 | 12/2001 | Colley et al. |
| 6,342,068 B1 | 1/2002 | Thompson |
| 6,344,041 B1 | 2/2002 | Kupiecki et al. |
| 6,344,048 B1 | 2/2002 | Chin et al. |
| 6,346,117 B1 | 2/2002 | Greenhalgh |
| 6,350,270 B1 | 2/2002 | Roue |
| 6,361,558 B1 * | 3/2002 | Hieshima et al. ............ 623/1.16 |
| 6,368,339 B1 | 4/2002 | Amplatz |
| 6,375,668 B1 | 4/2002 | Gifford et al. |
| 6,383,174 B1 | 5/2002 | Eder |
| 6,391,037 B1 | 5/2002 | Greenhalgh |
| 6,409,750 B1 | 6/2002 | Hyodoh et al. |
| 6,428,558 B1 | 8/2002 | Jones et al. |
| 6,443,972 B1 | 9/2002 | Bosma et al. |
| 6,447,531 B1 | 9/2002 | Amplatz |
| 6,454,780 B1 | 9/2002 | Wallace |
| 6,506,204 B2 | 1/2003 | Mazzocchi |
| 6,511,468 B1 | 1/2003 | Cragg et al. |
| 6,530,934 B1 | 3/2003 | Jacobsen et al. |
| 6,547,804 B2 | 4/2003 | Porter et al. |
| 6,551,303 B1 | 4/2003 | Van Tassel et al. |
| 6,569,179 B2 | 5/2003 | Teoh et al. |
| 6,579,303 B2 | 6/2003 | Amplatz |
| 6,585,748 B1 | 7/2003 | Jeffree |
| 6,585,756 B1 | 7/2003 | Strecker |
| 6,589,256 B2 | 7/2003 | Forber |
| 6,589,265 B1 | 7/2003 | Palmer et al. |
| 6,592,605 B2 | 7/2003 | Lenker et al. |
| 6,599,308 B2 | 7/2003 | Amplatz |
| 6,605,102 B1 | 8/2003 | Mazzocchi et al. |
| 6,605,111 B2 | 8/2003 | Bose et al. |
| 6,607,551 B1 | 8/2003 | Sullivan et al. |
| 6,613,074 B1 | 9/2003 | Mitelberg et al. |
| 6,626,939 B1 | 9/2003 | Burnside et al. |
| 6,632,241 B1 | 10/2003 | Hancock et al. |
| 6,635,068 B1 | 10/2003 | Dubrul et al. |
| 6,635,069 B1 | 10/2003 | Teoh et al. |
| 6,652,555 B1 | 11/2003 | VanTassel et al. |
| 6,652,556 B1 | 11/2003 | VanTassel et al. |
| 6,666,882 B1 | 12/2003 | Bose et al. |
| 6,666,883 B1 | 12/2003 | Seguin et al. |
| 6,669,717 B2 | 12/2003 | Marotta et al. |
| 6,669,721 B1 | 12/2003 | Bose et al. |
| 6,676,696 B1 | 1/2004 | Marotta et al. |
| 6,682,505 B2 | 1/2004 | Bates et al. |
| 6,682,546 B2 | 1/2004 | Amplatz |
| 6,689,150 B1 | 2/2004 | VanTassel et al. |
| 6,689,486 B2 | 2/2004 | Ho et al. |
| 6,695,876 B1 | 2/2004 | Marotta et al. |
| 6,698,877 B2 | 3/2004 | Urlaub et al. |
| 6,699,274 B2 | 3/2004 | Stinson |
| 6,712,835 B2 | 3/2004 | Mazzocchi et al. |
| 6,723,112 B2 | 4/2004 | Ho et al. |
| 6,723,116 B2 | 4/2004 | Taheri |
| 6,730,108 B2 | 5/2004 | Van Tassel et al. |
| 6,746,468 B1 | 6/2004 | Spetka et al. |
| 6,746,890 B2 | 6/2004 | Gupta et al. |
| 6,780,196 B2 | 8/2004 | Chin et al. |
| 6,792,979 B2 | 9/2004 | Konya et al. |
| 6,797,083 B2 | 9/2004 | Peterson |
| 6,802,851 B2 | 10/2004 | Jones et al. |
| RE38,653 E | 11/2004 | Igaki et al. |
| 6,811,560 B2 | 11/2004 | Jones et al. |
| 6,855,153 B2 | 2/2005 | Saadat |
| 6,855,154 B2 | 2/2005 | Abdel-Gawwad |
| RE38,711 E | 3/2005 | Igaki et al. |
| 6,860,893 B2 | 3/2005 | Wallace et al. |
| 6,936,055 B1 | 8/2005 | Ken et al. |
| 6,949,103 B2 | 9/2005 | Mazzocchi et al. |
| 6,949,113 B2 | 9/2005 | Van Tassel et al. |
| 6,953,472 B2 | 10/2005 | Palmer et al. |
| 6,979,341 B2 | 12/2005 | Scribner et al. |
| 6,989,019 B2 | 1/2006 | Mazzocchi et al. |
| 6,994,092 B2 | 2/2006 | van der Burg et al. |
| 6,994,717 B2 | 2/2006 | Konya et al. |
| 7,011,671 B2 | 3/2006 | Welch |
| 7,018,401 B1 | 3/2006 | Hyodoh et al. |
| 7,029,487 B2 | 4/2006 | Greene, Jr. et al. |

(56) References Cited

U.S. PATENT DOCUMENTS

| | | |
|---|---|---|
| 7,033,375 B2 | 4/2006 | Mazzocchi et al. |
| 7,048,752 B2 | 5/2006 | Mazzocchi et al. |
| 7,063,679 B2 | 6/2006 | Maguire et al. |
| 7,070,607 B2 | 7/2006 | Murayama et al. |
| 7,070,609 B2 | 7/2006 | West |
| 7,083,632 B2 | 8/2006 | Avellanet et al. |
| 7,128,073 B1 | 10/2006 | van der Burg et al. |
| 7,128,736 B1 | 10/2006 | Abrams et al. |
| 7,169,177 B2 | 1/2007 | Obara |
| 7,195,636 B2 | 3/2007 | Avellanet et al. |
| 7,211,109 B2 | 5/2007 | Thompson |
| 7,229,461 B2 | 6/2007 | Chin et al. |
| 7,232,461 B2 | 6/2007 | Ramer |
| 7,261,720 B2 | 8/2007 | Stevens et al. |
| 7,303,571 B2 | 12/2007 | Makower et al. |
| 7,306,622 B2 | 12/2007 | Jones et al. |
| 7,331,980 B2 | 2/2008 | Dubrul et al. |
| 7,367,985 B2 | 5/2008 | Mazzocchi et al. |
| 7,367,986 B2 | 5/2008 | Mazzocchi et al. |
| 7,371,250 B2 | 5/2008 | Mazzocchi et al. |
| 7,404,820 B2 | 7/2008 | Mazzocchi et al. |
| 7,410,482 B2 | 8/2008 | Murphy et al. |
| 7,410,492 B2 | 8/2008 | Mazzocchi et al. |
| 7,413,622 B2 | 8/2008 | Peterson |
| 7,419,503 B2 | 9/2008 | Pulnev et al. |
| 7,442,200 B2 | 10/2008 | Mazzocchi et al. |
| 7,485,088 B2 | 2/2009 | Murphy et al. |
| 7,556,635 B2 | 7/2009 | Mazzocchi et al. |
| 7,566,338 B2 | 7/2009 | Mazzocchi et al. |
| 7,569,066 B2 | 8/2009 | Gerberding et al. |
| 7,572,273 B2 | 8/2009 | Mazzocchi et al. |
| 7,572,288 B2 | 8/2009 | Cox |
| 7,597,704 B2 | 10/2009 | Frazier et al. |
| 7,608,088 B2 | 10/2009 | Jones et al. |
| 7,621,928 B2 | 11/2009 | Thramann et al. |
| 7,670,355 B2 | 3/2010 | Mazzocchi et al. |
| 7,670,356 B2 | 3/2010 | Mazzocchi et al. |
| 7,678,130 B2 | 3/2010 | Mazzocchi et al. |
| 7,682,390 B2 | 3/2010 | Seguin |
| 7,691,124 B2 | 4/2010 | Balgobin |
| 7,695,488 B2 | 4/2010 | Berenstein et al. |
| 7,699,056 B2 | 4/2010 | Tran et al. |
| 7,727,189 B2 | 6/2010 | VanTassel et al. |
| 7,744,583 B2 | 6/2010 | Seifert et al. |
| 7,744,652 B2 | 6/2010 | Morsi |
| 7,763,011 B2 | 7/2010 | Ortiz et al. |
| 7,828,815 B2 | 11/2010 | Mazzocchi et al. |
| 7,828,816 B2 | 11/2010 | Mazzocchi et al. |
| 7,906,066 B2 | 3/2011 | Wilson et al. |
| 7,922,732 B2 | 4/2011 | Mazzocchi et al. |
| 7,955,343 B2 | 6/2011 | Makower et al. |
| 7,972,359 B2 | 7/2011 | Kreidler |
| 7,993,364 B2 | 8/2011 | Morsi |
| RE42,758 E | 9/2011 | Ken et al. |
| 8,062,379 B2 | 11/2011 | Morsi |
| 8,075,585 B2 | 12/2011 | Lee et al. |
| 8,142,456 B2 | 3/2012 | Rosqueta et al. |
| 8,202,280 B2 | 6/2012 | Richter |
| 8,221,445 B2 | 7/2012 | van Tassel et al. |
| 8,261,648 B1 | 9/2012 | Marchand et al. |
| 8,298,257 B2 | 10/2012 | Sepetka et al. |
| 8,430,012 B1 | 4/2013 | Marchand et al. |
| 2001/0000797 A1 | 5/2001 | Mazzocchi |
| 2001/0012949 A1 | 8/2001 | Forber |
| 2001/0051822 A1 | 12/2001 | Stack et al. |
| 2002/0013599 A1 | 1/2002 | Limon et al. |
| 2002/0013618 A1 | 1/2002 | Marotta et al. |
| 2002/0042628 A1 | 4/2002 | Chin et al. |
| 2002/0062091 A1 | 5/2002 | Jacobsen et al. |
| 2002/0165572 A1 | 11/2002 | Saadat |
| 2002/0169473 A1 | 11/2002 | Sepetka et al. |
| 2003/0004538 A1 | 1/2003 | Secrest et al. |
| 2003/0028209 A1 | 2/2003 | Teoh et al. |
| 2003/0057156 A1 | 3/2003 | Peterson et al. |
| 2003/0171739 A1 | 9/2003 | Murphy et al. |
| 2003/0176884 A1 | 9/2003 | Berrada et al. |
| 2003/0195553 A1 | 10/2003 | Wallace et al. |
| 2003/0199913 A1 | 10/2003 | Dubrul et al. |
| 2003/0199919 A1 | 10/2003 | Palmer et al. |
| 2004/0015224 A1 | 1/2004 | Armstrong et al. |
| 2004/0034386 A1 | 2/2004 | Fulton et al. |
| 2004/0044391 A1 | 3/2004 | Porter |
| 2004/0098027 A1 | 5/2004 | Teoh et al. |
| 2004/0098030 A1 | 5/2004 | Makower et al. |
| 2004/0106945 A1 | 6/2004 | Thramann et al. |
| 2004/0106977 A1 | 6/2004 | Sullivan et al. |
| 2004/0111112 A1 | 6/2004 | Hoffmann |
| 2004/0122467 A1 | 6/2004 | VanTassel et al. |
| 2004/0122468 A1 | 6/2004 | Yodfat et al. |
| 2004/0143286 A1 | 7/2004 | Johnson et al. |
| 2004/0162606 A1 | 8/2004 | Thompson |
| 2004/0172056 A1 | 9/2004 | Guterman et al. |
| 2004/0181253 A1 | 9/2004 | Sepetka et al. |
| 2004/0186562 A1 | 9/2004 | Cox |
| 2004/0193206 A1 | 9/2004 | Gerberding et al. |
| 2004/0215332 A1 | 10/2004 | Frid |
| 2004/0249408 A1 | 12/2004 | Murphy et al. |
| 2004/0267346 A1 | 12/2004 | Shelso |
| 2005/0010281 A1 | 1/2005 | Yodfat et al. |
| 2005/0021077 A1 | 1/2005 | Chin et al. |
| 2005/0033408 A1 | 2/2005 | Jones et al. |
| 2005/0033409 A1 | 2/2005 | Burke et al. |
| 2005/0060017 A1 | 3/2005 | Fischell et al. |
| 2005/0096728 A1 | 5/2005 | Ramer |
| 2005/0096732 A1 | 5/2005 | Marotta et al. |
| 2005/0107823 A1 | 5/2005 | Leone et al. |
| 2005/0131443 A1 | 6/2005 | Abdel-Gawwad |
| 2005/0228434 A1 | 10/2005 | Amplatz et al. |
| 2005/0267568 A1 | 12/2005 | Berez et al. |
| 2005/0273135 A1 | 12/2005 | Chanduszko et al. |
| 2006/0052816 A1 | 3/2006 | Bates et al. |
| 2006/0064151 A1 | 3/2006 | Guterman et al. |
| 2006/0106421 A1 | 5/2006 | Teoh |
| 2006/0116713 A1 | 6/2006 | Sepetka et al. |
| 2006/0116714 A1 | 6/2006 | Sepetka et al. |
| 2006/0155323 A1 | 7/2006 | Porter et al. |
| 2006/0167494 A1 | 7/2006 | Suddaby |
| 2006/0190070 A1 | 8/2006 | Dieck et al. |
| 2006/0190076 A1 | 8/2006 | Taheri |
| 2006/0206199 A1 | 9/2006 | Churchwell et al. |
| 2006/0206200 A1 | 9/2006 | Garcia et al. |
| 2006/0235464 A1 | 10/2006 | Avellanet et al. |
| 2006/0235501 A1 | 10/2006 | Igaki |
| 2006/0241690 A1 | 10/2006 | Amplatz et al. |
| 2006/0247680 A1 | 11/2006 | Amplatz et al. |
| 2006/0264905 A1 | 11/2006 | Eskridge et al. |
| 2006/0264907 A1 | 11/2006 | Eskridge et al. |
| 2006/0271149 A1 | 11/2006 | Berez et al. |
| 2006/0271153 A1 | 11/2006 | Garcia et al. |
| 2006/0276827 A1 | 12/2006 | Mitelberg et al. |
| 2006/0292206 A1 | 12/2006 | Kim et al. |
| 2006/0293744 A1 | 12/2006 | Peckham et al. |
| 2007/0005125 A1 | 1/2007 | Berenstein et al. |
| 2007/0016243 A1 | 1/2007 | Ramaiah et al. |
| 2007/0021816 A1 | 1/2007 | Rudin |
| 2007/0088387 A1 | 4/2007 | Eskridge et al. |
| 2007/0093889 A1 | 4/2007 | Wu et al. |
| 2007/0106311 A1 | 5/2007 | Wallace et al. |
| 2007/0135826 A1 | 6/2007 | Zaver et al. |
| 2007/0150045 A1* | 6/2007 | Ferrera .................. 623/1.11 |
| 2007/0162104 A1 | 7/2007 | Frid |
| 2007/0173928 A1 | 7/2007 | Morsi |
| 2007/0191884 A1 | 8/2007 | Eskridge et al. |
| 2007/0191924 A1 | 8/2007 | Rudakov |
| 2007/0198075 A1 | 8/2007 | Levy |
| 2007/0203567 A1 | 8/2007 | Levy |
| 2007/0219619 A1 | 9/2007 | Dieck et al. |
| 2007/0221230 A1 | 9/2007 | Thompson et al. |
| 2007/0225760 A1 | 9/2007 | Moszner et al. |
| 2007/0225794 A1 | 9/2007 | Thramann et al. |
| 2007/0233244 A1 | 10/2007 | Lopez et al. |
| 2007/0239261 A1 | 10/2007 | Bose et al. |
| 2007/0265656 A1 | 11/2007 | Amplatz et al. |
| 2007/0270902 A1 | 11/2007 | Slazas et al. |

(56) References Cited

U.S. PATENT DOCUMENTS

| | | |
|---|---|---|
| 2007/0288083 A1 | 12/2007 | Hines |
| 2008/0009934 A1 | 1/2008 | Schneider et al. |
| 2008/0021535 A1 | 1/2008 | Leopold et al. |
| 2008/0039933 A1 | 2/2008 | Yodfat et al. |
| 2008/0045996 A1 | 2/2008 | Makower et al. |
| 2008/0045997 A1 | 2/2008 | Balgobin et al. |
| 2008/0058856 A1 | 3/2008 | Ramaiah et al. |
| 2008/0065145 A1 | 3/2008 | Carpenter |
| 2008/0097495 A1 | 4/2008 | Feller, III et al. |
| 2008/0109063 A1 | 5/2008 | Hancock et al. |
| 2008/0114391 A1 | 5/2008 | Dieck et al. |
| 2008/0114436 A1 | 5/2008 | Dieck et al. |
| 2008/0114439 A1 | 5/2008 | Ramaiah et al. |
| 2008/0119886 A1 | 5/2008 | Greenhalgh et al. |
| 2008/0125806 A1 | 5/2008 | Mazzocchi et al. |
| 2008/0140177 A1 | 6/2008 | Hines |
| 2008/0154286 A1 | 6/2008 | Abbott et al. |
| 2008/0195139 A1 | 8/2008 | Donald et al. |
| 2008/0219533 A1 | 9/2008 | Grigorescu |
| 2008/0221600 A1 | 9/2008 | Dieck et al. |
| 2008/0249562 A1 | 10/2008 | Cahill |
| 2008/0281350 A1 | 11/2008 | Sepetka et al. |
| 2008/0319533 A1 | 12/2008 | Lehe |
| 2009/0025820 A1 | 1/2009 | Adams |
| 2009/0069806 A1 | 3/2009 | De La Mora Levy et al. |
| 2009/0082803 A1 | 3/2009 | Adams et al. |
| 2009/0099647 A1 | 4/2009 | Glimsdale et al. |
| 2009/0112251 A1 | 4/2009 | Qian et al. |
| 2009/0118811 A1 | 5/2009 | Moloney |
| 2009/0143851 A1 | 6/2009 | Paul, Jr. |
| 2009/0198315 A1 | 8/2009 | Boudjemline |
| 2009/0210047 A1 | 8/2009 | Amplatz et al. |
| 2009/0216307 A1 | 8/2009 | Kaufmann et al. |
| 2009/0228029 A1 | 9/2009 | Lee |
| 2009/0259202 A1 | 10/2009 | Leeflang et al. |
| 2009/0264914 A1* | 10/2009 | Riina et al. .................. 606/191 |
| 2009/0275974 A1 | 11/2009 | Marchand et al. |
| 2009/0287291 A1 | 11/2009 | Becking et al. |
| 2009/0287294 A1 | 11/2009 | Rosqueta et al. |
| 2009/0287297 A1 | 11/2009 | Cox |
| 2009/0318941 A1 | 12/2009 | Sepetka et al. |
| 2010/0004726 A1 | 1/2010 | Hancock et al. |
| 2010/0004761 A1 | 1/2010 | Flanders et al. |
| 2010/0023105 A1 | 1/2010 | Levy et al. |
| 2010/0030200 A1 | 2/2010 | Strauss et al. |
| 2010/0030220 A1 | 2/2010 | Truckai et al. |
| 2010/0042133 A1 | 2/2010 | Ramzipoor et al. |
| 2010/0069948 A1 | 3/2010 | Veznedaroglu et al. |
| 2010/0094335 A1 | 4/2010 | Gerberding et al. |
| 2010/0131002 A1 | 5/2010 | Connor et al. |
| 2010/0152767 A1 | 6/2010 | Greenhalgh et al. |
| 2010/0268260 A1 | 10/2010 | Riina et al. |
| 2010/0274276 A1 | 10/2010 | Chow et al. |
| 2010/0312270 A1 | 12/2010 | McGuckin, Jr. et al. |
| 2010/0331948 A1 | 12/2010 | Turovskiy et al. |
| 2011/0022149 A1 | 1/2011 | Cox et al. |
| 2011/0144669 A1 | 6/2011 | Becking et al. |
| 2011/0152993 A1 | 6/2011 | Marchand et al. |
| 2011/0184453 A1 | 7/2011 | Levy et al. |
| 2011/0196415 A1 | 8/2011 | Ujiie et al. |
| 2011/0202085 A1 | 8/2011 | Loganathan et al. |
| 2011/0208227 A1 | 8/2011 | Becking |
| 2011/0245862 A1 | 10/2011 | Dieck et al. |
| 2011/0265943 A1 | 11/2011 | Rosqueta et al. |
| 2011/0313447 A1 | 12/2011 | Strauss et al. |
| 2011/0319926 A1 | 12/2011 | Becking et al. |
| 2012/0041470 A1 | 2/2012 | Shrivastava et al. |
| 2012/0065720 A1 | 3/2012 | Strauss et al. |
| 2012/0143237 A1 | 6/2012 | cam et al. |
| 2012/0143317 A1 | 6/2012 | Cam et al. |
| 2012/0165803 A1 | 6/2012 | Bencini et al. |
| 2012/0165919 A1 | 6/2012 | Cox et al. |
| 2012/0197283 A1 | 8/2012 | Marchand et al. |
| 2012/0245674 A1 | 9/2012 | Molaei et al. |
| 2012/0245675 A1 | 9/2012 | Molaei et al. |
| 2012/0283768 A1 | 11/2012 | Cox et al. |
| 2012/0316598 A1 | 12/2012 | Becking et al. |
| 2012/0330341 A1 | 12/2012 | Becking et al. |
| 2012/0330347 A1 | 12/2012 | Becking et al. |
| 2013/0066360 A1 | 3/2013 | Becking et al. |
| 2013/0085522 A1 | 4/2013 | Becking et al. |
| 2013/0092013 A1 | 4/2013 | Thompson et al. |
| 2013/0123830 A1 | 5/2013 | Becking et al. |
| 2013/0211495 A1 | 8/2013 | Halden et al. |
| 2013/0233160 A1 | 9/2013 | Marchand et al. |
| 2013/0239790 A1 | 9/2013 | Thompson et al. |
| 2013/0245667 A1 | 9/2013 | Marchand et al. |
| 2013/0268053 A1 | 10/2013 | Molaei et al. |
| 2013/0274862 A1 | 10/2013 | Cox et al. |
| 2013/0274863 A1 | 10/2013 | Cox et al. |
| 2013/0274866 A1 | 10/2013 | Cox et al. |
| 2013/0274868 A1 | 10/2013 | Cox et al. |

FOREIGN PATENT DOCUMENTS

| | | |
|---|---|---|
| EP | 775470 | 5/1997 |
| EP | 855170 A2 | 7/1998 |
| EP | 1621148 | 2/2006 |
| EP | 1637176 | 3/2006 |
| EP | 1752112 | 2/2007 |
| EP | 1942972 | 7/2008 |
| EP | 1872742 B1 | 5/2009 |
| EP | 2279023 A2 | 2/2011 |
| EP | 2363075 | 9/2011 |
| EP | 2496299 A2 | 9/2012 |
| EP | 2675402 A2 | 12/2013 |
| FR | 2556210 B1 | 4/1988 |
| FR | 2890306 | 3/2007 |
| JP | 11-506686 | 6/1999 |
| JP | 2003520103 A | 7/2003 |
| JP | 2003-524434 A | 8/2003 |
| JP | 2004-049585 A | 2/2004 |
| JP | 2005-522266 A | 7/2005 |
| JP | 2006-506201 A | 2/2006 |
| JP | 2008-541832 A | 11/2008 |
| JP | 4673987 B2 | 4/2011 |
| WO | WO-88/00813 | 2/1988 |
| WO | WO-96/01591 | 1/1996 |
| WO | WO-97/26939 | 7/1997 |
| WO | WO-99/03404 | 1/1999 |
| WO | WO 99/05977 | 2/1999 |
| WO | WO-99/08607 | 2/1999 |
| WO | WO 99/08743 | 2/1999 |
| WO | WO-99/62432 | 12/1999 |
| WO | WO 01/93782 | 12/2001 |
| WO | WO 02/00139 | 1/2002 |
| WO | WO-02/071977 A2 | 9/2002 |
| WO | WO-2005/117718 | 12/2005 |
| WO | WO-2006/026744 | 3/2006 |
| WO | WO-2006/034166 A2 | 3/2006 |
| WO | WO-2006/052322 A2 | 5/2006 |
| WO | WO-2006/091891 A2 | 8/2006 |
| WO | WO-2006/119422 A2 | 11/2006 |
| WO | WO-2007/047851 A2 | 4/2007 |
| WO | WO 2007/076480 | 7/2007 |
| WO | WO-2007/121405 | 10/2007 |
| WO | WO 2008/022327 | 2/2008 |
| WO | WO 2008/151204 A1 | 12/2008 |
| WO | WO-2008/157507 A2 | 12/2008 |
| WO | WO 2009/076515 A1 | 6/2009 |
| WO | WO-2009/132045 A2 | 10/2009 |
| WO | WO-2009/134337 | 11/2009 |
| WO | WO-2009135166 A2 | 11/2009 |
| WO | WO-2010/028314 | 3/2010 |
| WO | WO-2010/030991 | 3/2010 |
| WO | WO-2011/057002 A2 | 5/2011 |
| WO | WO-2011/057277 A2 | 5/2011 |
| WO | WO-2011/130081 | 10/2011 |
| WO | WO-2011/153304 | 12/2011 |
| WO | WO-2012/112749 A2 | 8/2012 |

OTHER PUBLICATIONS

Thorell, et al., "Y-configured Dual Intracranial Stent-assisted Coil Embolization for the Treatment of Wide-necked Basilar Tip Aneu-

(56) References Cited

OTHER PUBLICATIONS rysms", Neurosurgery, May 2005, vol. 56, Issue 5, pp. 1035-1040.
U.S. Appl. No. 13/629,678, filed Sep. 28, 2012.
International Search Report and Written Opinion dated Apr. 12, 2011 for International Application No. PCT/US 11/23054.
International Preliminary Report on Patentability for International Application No. PCT/US2009/051316, dated Jan. 25, 2011.
International Search Report and Written Opinion for International Application No. PCT/US2009/051316, mailed on Nov. 23, 2009, in 17 pages.
Notification Concerning Transmittal of International Preliminary Report on Patentability for International Application No. PCT/US2009/051316; dated Feb. 3, 2011.
Hill, et al., "Initial Results of the AMPLATZER Vascular Plug in the Treatment of Congenital Heart Disease, Business Briefing," US Cardiology 2004.
Ronnen, "AMPLATZER Vascular Plug Case Study, Closure of Arteriovenous Fistula Between Deep Femoral Artery and Superficial Femoral Vein," AGA Medical Corporation, May 2007.
U.S. Appl. No. 13/669,652, filed Nov. 6, 2012.
U.S. Appl. No. 13/826,298, filed Mar. 14, 2013.
U.S. Appl. No. 13/795,556, filed Mar. 12, 2013.
U.S. Appl. No. 13/962,267, filed Aug. 8, 2013.

\* cited by examiner

VASCULAR REMODELING DEVICE

CROSS-REFERENCE TO RELATED APPLICATIONS

This application claims priority benefit of U.S. Provisional Patent Application No. 61/299,266, filed Jan. 28, 2010, which is incorporated herein by reference in its entirety.

BACKGROUND

1. Field

The present application generally relates to vascular remodeling devices and to the manner of their positioning in vessels, and, more particularly, to generally spherical remodeling devices and to the matter of their positioning at the junction of neurovascular bifurcations having an aneurysm.

2. Description of Related Art

Neurovascular or cerebral aneurysms affect about 5% of the population. Aneurysms may be located, for example, along arterial side walls (e.g., the aneurysm 10 illustrated in FIG. 1) and at arterial bifurcations (e.g., the aneurysm 20 illustrated in FIG. 2). The direction of fluid flow is generally indicated by the arrows 16, 26. The aneurysms 10, 20 each have a fundus 12, 22, a neck 14, 24, and a fundus-to-neck ratio or "neck ratio." If the neck ratio is greater than 2 to 1 or if the neck 14, 24 is less than 4 mm, the aneurysm 10, 20 may be treated with embolization coils alone because the coils will generally constrain themselves within the aneurysm 10, 20 without herniating into parent vessels. If the neck ratio is less than 2 to 1 or if the neck 14, 24 is greater than 4 mm, the aneurysms 10, 20 may be difficult to treat with embolization coils alone because the coils may be prone to herniating into parent vessels, as illustrated in FIGS. 3A and 3B. Herniation of coils may cause arterial occlusion, stroke, and/or death. Compared to the bifurcation illustrated in FIG. 2, the efferent vessels of the bifurcation may be at substantially different angles, have substantially different sizes, and/or be a different quantity (e.g., three or more). Compared to the bifurcation illustrated in FIG. 2, the aneurysm 20 of the bifurcation may be offset with respect to the junction (e.g., having a neck substantially open to one efferent vessel), tilted with respect to a plane created by the vessels (e.g., into or out of the page), etc. Each of these would still be accurately characterized as a "bifurcation" herein.

In order to inhibit such herniation, tubular neck remodeling devices, for example Neuroform™, available from Boston Scientific, and Enterprise™, available from Cordis Neurovascular, may be used to keep coils or other materials within the fundus of the aneurysm and out of the vessels. Tubular remodeling devices generally consist of a braided wire or cut metallic stent or stents covering the neck of the aneurysm so that materials introduced into the fundus of the aneurysm do not herniate out of the aneurysm. As illustrated in FIG. 4A, tubular remodeling devices 40 are generally useful for side wall aneurysms 10. As illustrated in FIGS. 4B and 4C, tubular remodeling devices 42, 44 are generally less useful for aneurysms 20 at bifurcations, for example because shaping the remodeling devices to preserve blood flow through the afferent and efferent vessels while also inhibiting herniation of coils 28 out of the aneurysm 20 can be difficult.

SUMMARY

In some embodiments described herein, a generally spherical vascular remodeling device is provided. The device is permanently positionable at a junction of afferent and efferent vessels of a bifurcation (e.g., a neurovascular bifurcation) having an aneurysm having a fundus and a neck. Positioning may comprise deployment from a catheter and mechanical or electrolytic release from the catheter. After positioning the device at the junction, the device can lock into place across the arterial ostia and the neck of the aneurysm, substantially conforming to the shape of the junction. After positioning the device at the junction, the device acts as a scaffolding to inhibit or prevent herniation or prolapse of objects such as embolization coils and thrombi out of the neck of the aneurysm. Embolic material may be inserted in the fundus of the aneurysm before or after positioning the device. After positioning the device at the junction, the device permits perfusion of fluid (e.g., blood) to the efferent vessels. The device may have a first end, a second end substantially opposite to the first end, and a plurality of polymer filaments extending between and coupled at the first end and the second end. Certain such devices may be football shaped, pumpkin shaped, or twisted. The polymer filaments may comprise bioabsorbable polymers (e.g., polylactic acid, polyglycolic acid, poly(lactic-co-glycolic acid), poly-epsilon-caprolactone, and/or naturally-derived bioabsorbable polymers). The device may comprise a plurality of loops (e.g., circular loops) or filaments forming a generally spherical shape, each loop comprising a bioabsorbable polymer (e.g., polylactic acid, polyglycolic acid, poly(lactic-co-glycolic acid), poly-epsilon-caprolactone, and/or naturally-derived bioabsorbable polymers). Radiopaque markers may be placed at one or both ends of the device and/or at least one of the loops or filaments may comprise a radiopaque material (e.g., platinum). In certain embodiments, a method of treating an aneurysm at a junction of a bifurcation having an afferent vessel and efferent vessels is provided. The aneurysm has a neck and a fundus. The method comprises advancing a catheter proximate to the junction of the bifurcation. The catheter at least partially contains a generally spherical vascular remodeling device in a compressed state. The device comprises a plurality of polymer filaments. The method further comprises positioning the device at the junction of the bifurcation and withdrawing the catheter and leaving the device at the junction of the bifurcation. The device acts as a scaffolding to inhibit herniation of objects out of the neck of the aneurysm after withdrawal of the delivery catheter. The device permits perfusion of fluid to the efferent vessels.

In certain embodiments, a generally spherical remodeling device comprises a first end, a second end substantially opposite to the first end, and a plurality of polymer filaments extending between the first end and the second end and coupled at the first end and the second end. The device is configured to be positioned at a junction of a bifurcation comprising at least one afferent vessel, efferent vessels, and an aneurysm having a neck after withdrawal of a delivery catheter. The device is configured to act as a scaffolding to inhibit herniation of objects out of the neck of the aneurysm. The device is configured to permit perfusion of fluid to the efferent vessels.

In certain embodiments, a remodeling device comprising a plurality of polymer arcuate loops forming a generally spherical shape is provided. The device is configured to be positioned at a junction of a bifurcation having an aneurysm after withdrawal of a delivery catheter. The device is configured to act as a scaffolding to inhibit matter from herniating out of the aneurysm. The device is configured to permit perfusion of blood to efferent vessels of the bifurcation.

For purposes of summarizing the invention and the advantages achieved over the prior art, certain objects and advantages of the invention are described herein. Of course, it is to be understood that not necessarily all such objects or advantages need to be achieved in accordance with any particular embodiment. Thus, for example, those skilled in the art will recognize that the invention may be embodied or carried out in a manner that achieves or optimizes one advantage or group of advantages as taught or suggested herein without necessarily achieving other objects or advantages as may be taught or suggested herein.

All of these embodiments are intended to be within the scope of the invention herein disclosed. These and other embodiments will become readily apparent to those skilled in the art from the following detailed description having reference to the attached figures, the invention not being limited to any particular disclosed embodiment(s).

BRIEF DESCRIPTION OF THE DRAWINGS

These and other features, aspects, and advantages of the present disclosure are described with reference to the drawings of certain embodiments, which are intended to illustrate certain embodiments and not to limit the invention.

DETAILED DESCRIPTION

Although certain embodiments and examples are described below, those of skill in the art will appreciate that the invention extends beyond the specifically disclosed embodiments and/or uses and obvious modifications and equivalents thereof. Thus, it is intended that the scope of the invention herein disclosed should not be limited by any particular embodiments described below.

Figure 5:
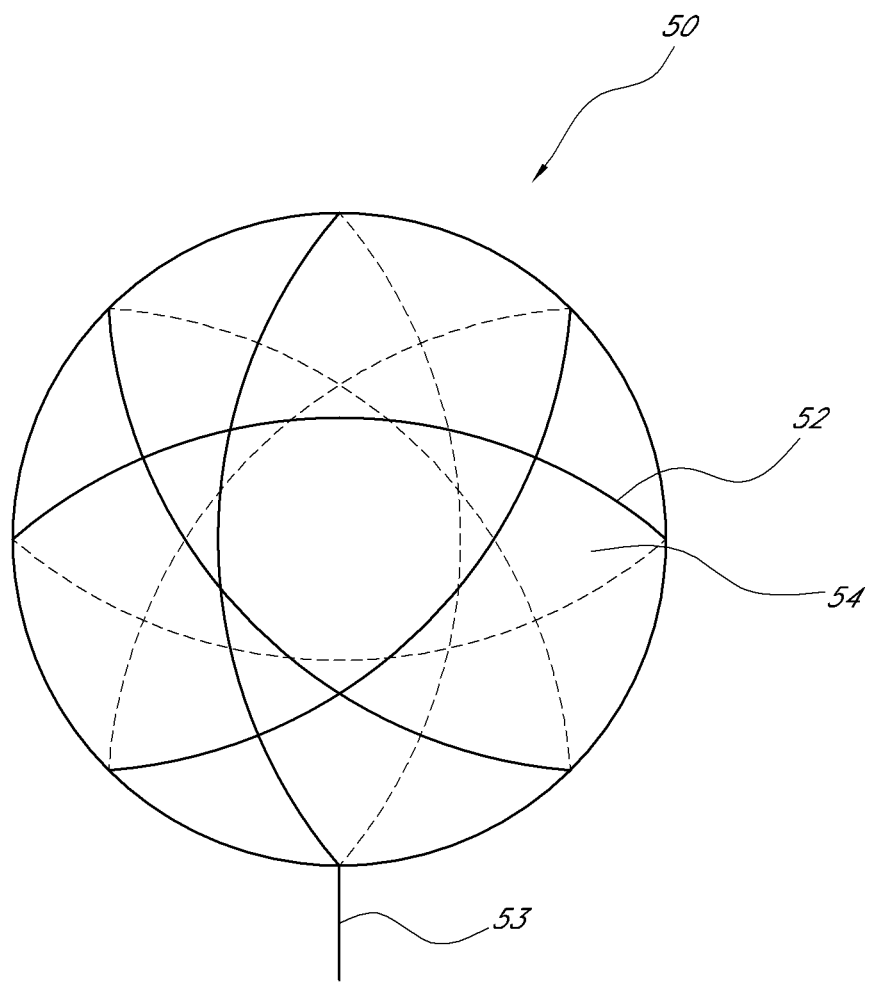
FIG. 5 illustrates an example embodiment of a generally spherical vascular remodeling device.

FIG. 5 illustrates an example embodiment of a generally spherical vascular remodeling device 50. It will be appreciated that the device 50 may be more compliant than the vasculature in which it is deployed such that it may be somewhat misshapen (e.g., non-spherical, for example as illustrated in FIG. 6B) after being deployed, and that the phrase "generally spherical" describes the shape of the device 50 when in an expanded (e.g., fully expanded) state. Additionally, the phrase "generally spherical" distinguishes the device 50, which is generally uniform in each dimension in an expanded state, from tubular stents having a small radial dimension and a large longitudinal dimension in an expanded state. In some embodiments of a generally spherical device, an outer periphery of the device has a shape that deviates by between about 10% and about 25% from an outer periphery of a mathematically perfect sphere. In some embodiments, the device 50 has a length and a width that are within less than about 33% of each other (e.g., having a length of 6 mm and a width of 8 mm, having a length of 6 mm and a width of 8 mm). Embodiments in which the width is greater than the length may be advantageous due to a difference in porosity at a midpoint and an end proximate to an aneurysm. Embodiments in which the length is greater than the width may be advantageous for positioning a portion of the device 50 in a portion of the aneurysm 20 (e.g., to aid in embolization).

Figure 7A:
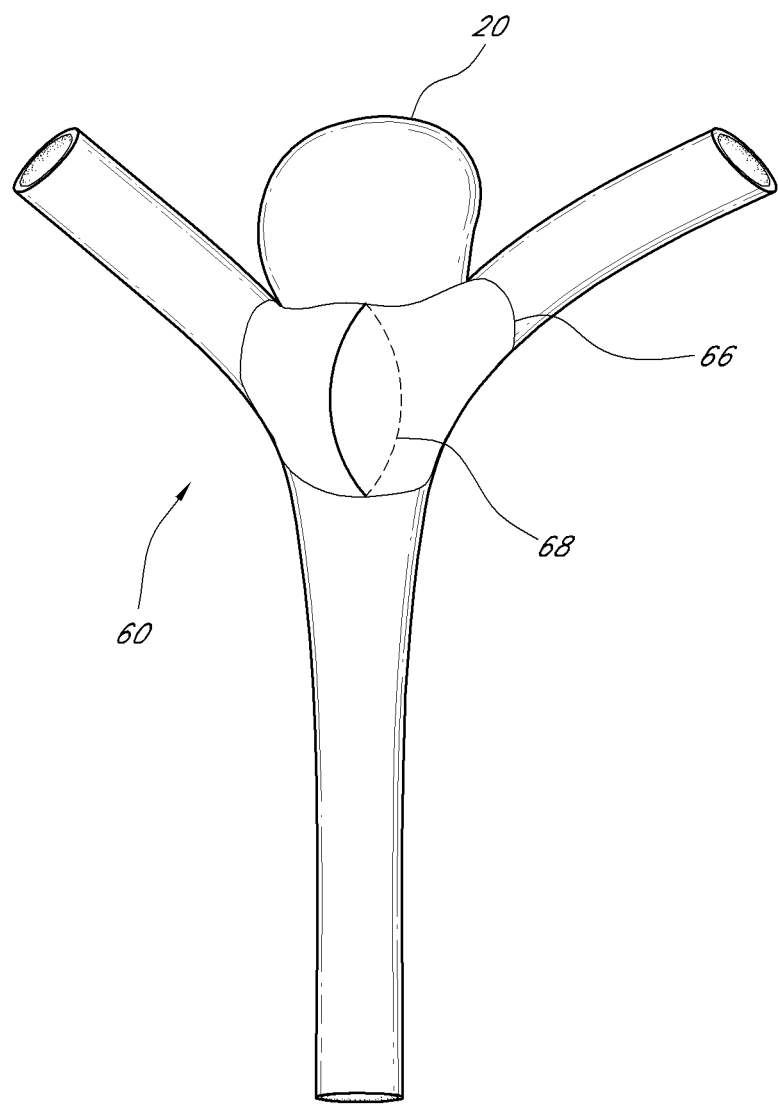
FIGS. 7A-7C illustrate another example embodiment of a method for treating an aneurysm using the device of FIG. 5.

In the embodiment illustrated in FIG. 5, the device 50 comprises a plurality of generally circular loops 52 coupled together. Coupling of the loops 52 may comprise adhering, welding, soldering, interlacing (e.g., some loops 52 being over or under other loops 52), intertwining, meshing, combinations thereof, and the like. In the embodiment illustrated in FIG. 5, the device 50 comprises a lead or tail 53, which may be used for releasing and/or retracting the device 50 after deployment, as described herein. In some embodiments, the device 50 comprises a cut metallic sphere, a single filament, a plurality of non-circular filaments (e.g., arcuate segments), etc. In some embodiments, each loop 52 forms a plane and the intersections of the planes are substantially parallel (e.g., as illustrated in FIG. 7A).

In some embodiments, at least some of the loops 52 or filaments comprise a self-expanding and/or a shape-memory material (e.g., comprising Nitinol, CoCr alloy, etc.), thereby causing the device 50 to be self-expanding under certain conditions (e.g., not restrained by a catheter). In some embodiments, at least one of the loops 52 comprises a different material than others of the loops 52 (e.g., some loops 52 comprising Nitinol and some loops 52 comprising Nitinol and platinum). In some embodiments, at least one of the loops 52 comprises a radiopaque material (e.g., platinum). In certain such embodiments, an even number of loops 52 (e.g., two, four, etc.) comprises a radiopaque material (e.g., platinum). In some embodiments, at least one of the loops 52 comprises a radiopaque material (e.g., platinum) at least partially wrapped (e.g., coiled) around a self-expanding material (e.g., Nitinol). In some embodiments, at least one of the loops 52 comprises a self-expanding material with a radiopaque core (e.g., Nitinol with a platinum core) or a radiopaque coating (e.g., Nitinol coated with platinum, tantalum, etc. by physical vapor deposition, chemical vapor deposition, plating, etc.). It will be appreciated that the amount and type of radiopaque material used may depend, inter alia, on price, desired level of radiopacity, mechanical properties of the radiopaque material, and corrosion properties of the radiopaque material. In certain embodiments, the loops 52 have a substantially circular or ovoid cross section (e.g., embodiments, in which the loops 52 comprise separate wires). In some embodiments, the loops 52 have a substantially rectangular or flat cross section (e.g., embodiments, in which the loops 52 comprise uncut portions of a metallic tube). Other shapes of loops 52 and combinations of shapes of loops 52 are also possible. In certain embodiments, the plurality of loops 52 comprises between about six and about twelve loops 52. In certain embodiments, the plurality of loops 52 comprises at least about six loops 52, at least about eight loops 52, or at least about twelve loops 52. Other numbers of loops 52 are also possible.

In certain embodiments, at least some of the loops 52 or filaments comprise a polymer. In some embodiments, at least some of the loops 52 or filaments comprise a polymer that is bioabsorbable. In certain embodiments, at least some of the loops 52 or filaments comprise polyglycolic acid (PGA), polylactic acid (PLA), poly(lactic-co-glycolic acid) (PLGA), poly-epsilon-caprolactone (PCL), naturally-derived bioabsorbable polymers (NDB), or combinations thereof (e.g., a first group of the loops 52 comprising PGA and a second group of the loops 52 comprising PLA, PLGA, PCL, and/or NDB, a first group of the loops 52 comprising PLA and a second group of the loops 52 comprising PGA, PLGA, PCL, and/or NDB, a first group of the loops 52 comprising PLGA and a second group of the loops 52 comprising PLA, PGA, PCL, and/or NDB, a first group of the loops 52 comprising PCL and a second group of the loops 52 comprising PGA, PLA, PLGA, and/or NDB, a first group of the loops 52 comprising NDB and a second group of the loops 52 comprising PGA, PLA, PLGA, and/or PCL, etc.). Other polymers are also possible. PGA, PLA, PLGA, PCL, and NDB are all bioabsorbable; however they have different rates of bioabsorption. The bioabsorption rates of a single polymer can also vary based on, for example, blood characteristics, blood flow, loop 52 dimensions, etc. PLA has the longest bioabsorption rate. In some embodiments, the bioabsorption rate of PLA is at least about ten months. In some embodiments, the bioabsorption rate of PLA is at least about one year. In some embodiments, the bioabsorption rate of PLA is at least about fourteen months. In some embodiments, the bioabsorption rate of PLA is between about 10 months and about 14 months (e.g., about one year). In some embodiments, the bioabsorption rate of PGA is between about 1 week and about 3 weeks. In some embodiments, the bioabsorption rate of PGA is between about 2 weeks and about 4 weeks. The bioabsorption rates of PLGA, PCL, and NDB are generally between the bioabsorption rates of PLA and PGA, and may depend on parameters such as, for example, molecular weight (e.g., generally the higher the molecular weight, the longer the bioabsorption rate), structure (e.g., depending on the arrangement of repeating units), etc. of the polymer. In some embodiments, PLGA, PCL, and NDB may have a bioabsorption rate between about 4 weeks and about 1 year. The bioabsorption rate generally refers to the time lose about 50% of strength. The polymer(s) used in the device 50 may be selected based on the amount of time an aneurysm may take to thrombose (e.g., based on fundus size, neck width, etc.). For example, if an aneurysm is expected to take one month to thrombose and the device 50 is expected to persist through thrombosis but not long thereafter, PGA may be selected. The polymer(s) used in the device 50 may be selected based on the amount of time an aneurysm may take to obliterate (e.g., based on fundus size, neck width, etc.). For example, if an aneurysm is expected to take one year to obliterate and the device 50 is expected to persist through obliteration, PLA may be selected. Other polymers or combinations of polymers can be selected based on the particular aneurysm to be treated and the desired action and/or persistence of the device 50 with respect to the aneurysm. Other selection criteria are also possible. Different combinations of polymers with different rates of bioabsorption can allow for selection of a desired rate of bioabsorption for the device 50. For example, a device 50 with a combination of PGA and PLA loops 52 may have a rate of bioabsorption in between the rate of bioabsorption of a device 50 comprising only loops 52 comprising PGA and the rate of bioabsorption of a device 50 comprising only loops 52 comprising PLA.

In certain embodiments, the device 50 is configured to be positioned at a junction of a bifurcation (e.g., a neurovascular bifurcation) comprising at least one afferent vessel, efferent vessels, and an aneurysm having a fundus and a neck. For example, in some embodiments, the device 50 is suitably dimensioned to fit in a junction of a bifurcation (e.g., having a diameter between about 2 mm and about 12 mm, having a diameter between about 6 mm and about 8 mm, having a diameter less than about 12 mm, having a diameter greater than about 2 mm). For another example, in some embodiments, the device 50 is less rigid than a junction of a bifurcation (e.g., due to the number of loops 52, the material of the loops 52, the thickness of the loops 52, the spacing of the loops 52, the shape of the loops 52, combinations thereof, and the like). In certain embodiments, the device 50 is configured to act as a scaffolding to inhibit or prevent herniation or prolapse of objects (e.g., embolization coils, thrombi, etc.) out of a neck of an aneurysm. For example, in some embodiments, the loops 52 are dense enough at the neck of the aneurysm that objects cannot pass. In certain embodiments, the device 50 is configured to permit perfusion of fluid (e.g., blood) to efferent vessels of a bifurcation. For example, in some embodiments, the device 50 is substantially devoid of a covering, mesh, or other material between the loops 52, thereby allowing fluid to flow substantially unimpeded.

The device 50 comprises a plurality of perforations or cells 54 between the loops 52. In certain embodiments, a percentage of the outer surface of the device 50 covered by the loops 52 is between about 25% and about 40%. In certain embodiments, a percentage of the outer surface of the device 50 covered by the cells 54 is between about 60% and about 75%. Other porosities are also possible. In some embodiments (e.g., in embodiments in which the device 50 comprises loops 52 that form a plane and in which the intersections of the planes are substantially parallel (e.g., as illustrated in FIG. 7A)), porosity distally increases between a proximal end of the device 50 and an approximate midpoint and distally decreases between the approximate midpoint and a distal end of the device 50. In some embodiments, the device 50 further comprises one or more radiopaque markers (e.g., comprising or at least partially covering a portion of a loop 52, at a proximal end of the device 50, at a distal end of the device 50, etc.).

Figure 6A:
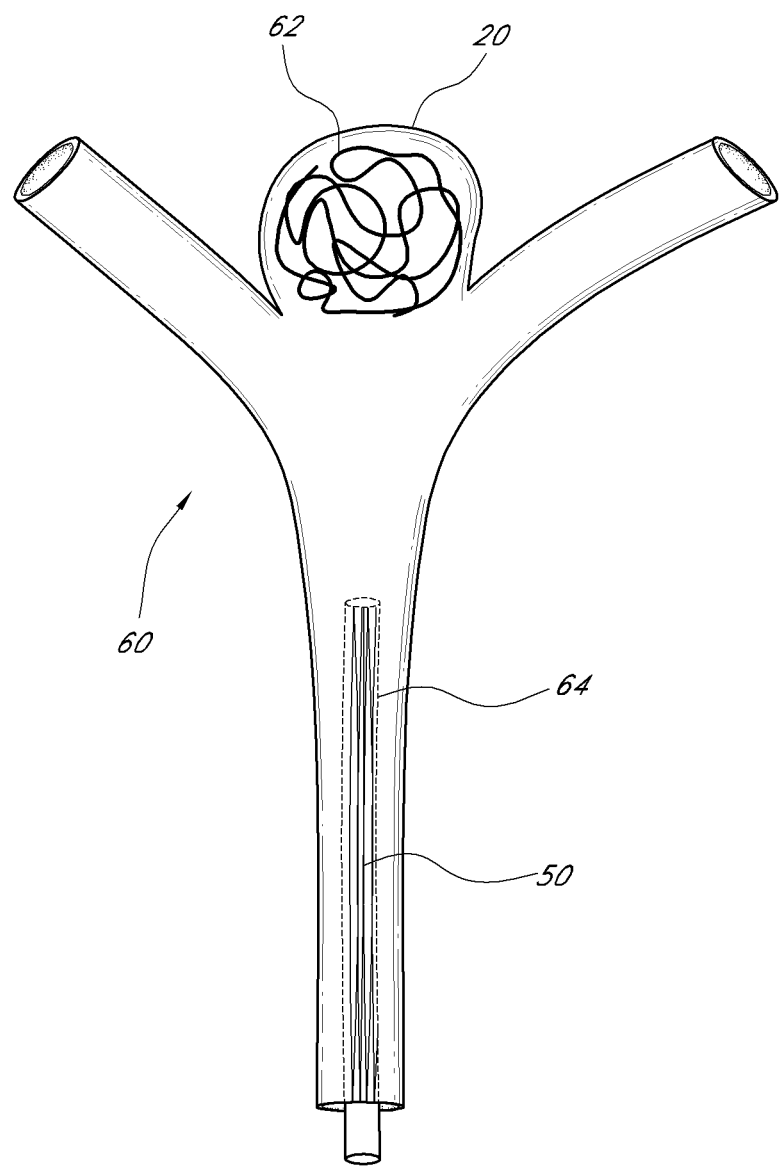
FIGS. 6A-6C illustrate an example embodiment of a method for treating an aneurysm using the device of FIG. 5.
Figure 6B:
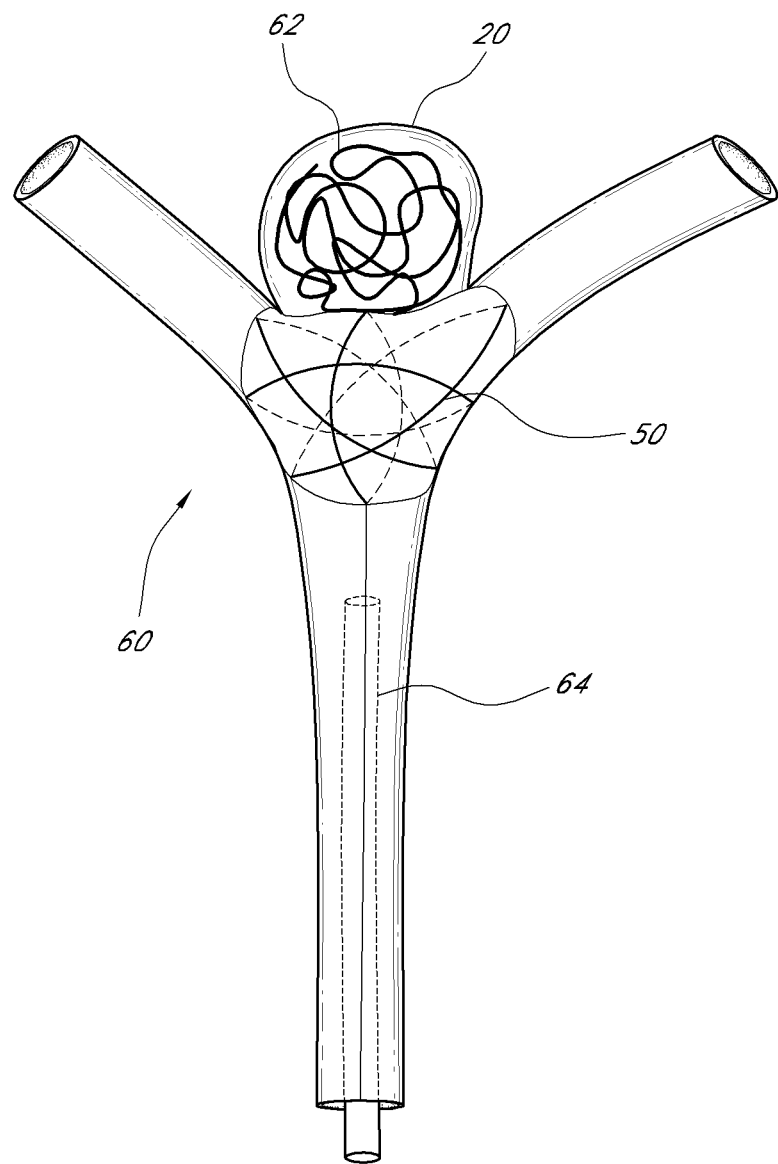
Figure 6C:
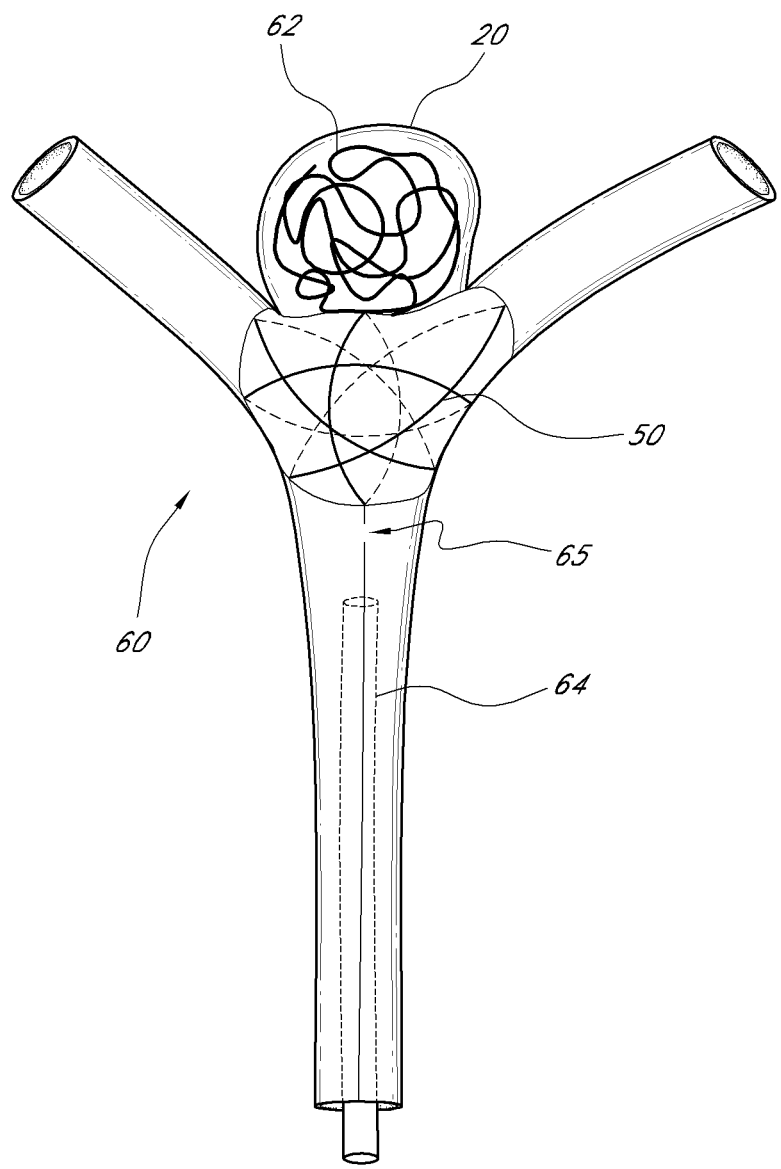

FIGS. 6A-6C illustrate an example embodiment of a method for treating an aneurysm 20 using the device 50. FIG. 6A illustrates a confluence of afferent and efferent vessels or "junction" at a bifurcation 60 having an aneurysm 20. In some embodiments, the vessels are neurovascular or cranial. The aneurysm 20 is illustrated with a plurality of embolization coils 62 having been inserted in the fundus 22 of the aneurysm 20. It will be appreciated that the embolization coils 62 may be a single embolization coil or other embolic material. A catheter 64 (e.g., a microcatheter), at least partially containing a constricted or compressed device 50, is also shown in the afferent vessel. The catheter 64 is small enough and flexible enough to be routed through the vasculature and situated proximate to the aneurysm 20. In some embodiments, the embolization coils 62 are inserted in the fundus 22 of the aneurysm 20 using the catheter 64. In some embodiments, the embolization coils 62 are inserted in the fundus 22 of the aneurysm 20 using a different catheter. In certain such embodiments, a guidewire may be used to guide both catheters.

FIG. 6B illustrates the bifurcation 60 after the device 50 has been deployed from the catheter 64 (e.g., by being pushed out with a plunger, by retracting the catheter 64 while the device 50 remains stationary, etc.). After being deployed from the catheter 64, the device 50 may expand. In some embodiments, the device 50 comprises a self-expanding and/or a shape-memory material that automatically expands towards an uncompressed state or does so upon the application of warm fluid (e.g., saline). The device 50 may substantially conform to the shape of the junction of the bifurcation 60 (e.g., not substantially including portions extending into the afferent and efferent vessels) and locks into place across the ostia of the afferent and efferent vessels and the neck 24 of the aneurysm 20. The device 50 at least partially covers the neck 24 of the aneurysm 20 as well as the afferent and efferent vessels, but does not need to divert flow. The device 50 acts as a scaffolding to inhibit or prevent herniation or prolapse of objects such as the embolization coils 62 and/or thrombi out of the aneurysm 24. The device 50 also allows perfusion of fluid (e.g., blood) from the afferent vessel(s) to the efferent vessel(s).

FIG. 6C illustrates the bifurcation 60 after the device 50 has been released from the catheter 64. In some embodiments, the device 50 is released mechanically (e.g., by a release mechanism). In some embodiments, the device 50 is released electrolytically (e.g., by applying a small current until a portion of the tail 53 proximal to the device 50 corrodes away, as illustrated by the gap 65). The catheter 64 is then withdrawn from the bifurcation 60, thereby leaving or permanently positioning the device 50 at the junction of the bifurcation 60.

It will be appreciated that the term "permanently" does not mean that the device 50 is impossible to remove at a later time. In some embodiments, the device 50 may be retracted into the catheter 64 after being deployed from the catheter 64 (e.g., by pulling on the tail 53). The device 50 may then be deployed, for example at a new angle, at a new rotational position, more proximal or distal to an afferent vessel and/or an efferent vessel, etc. For example, although the device 50 expands towards an uncompressed state after deployment, the resulting shape of the device 50 at the junction of the bifurcation 60 may vary depending on the details of the deployment from the catheter 64 because the device 50 adapts to the shape of the anatomy (e.g., due to the size, shape, number, etc. of the loops 52). Once the user is satisfied with properties of the device 50 (e.g., position, tilt, rotation, shape, interaction with the vessels, etc.), the device 50 may be released as described herein.

Combinations of the steps described above are also possible. In some embodiments, the embolization coils 62 may be inserted in the fundus 22 of the aneurysm 20 after the device 50 has been deployed from the catheter 64 (e.g., using the catheter 64 to insert the embolization coils 62). In some embodiments, the embolization coils 62 may be inserted in the fundus 22 of the aneurysm 20 after the device 50 has been released from the catheter 64 (e.g., using the catheter 64 to insert the embolization coils 62).

In certain embodiments, the loops 52 or filaments comprise a bioabsorbable polymer. This bioabsorbability can be advantageous in conjunction with permanent placement of the device 50. For example, after thrombosis of the aneurysm following treatment, the device 50 may no longer be needed to inhibit herniation of material. Certain bioabsorbable embodiments of the device 50 may advantageously inhibit herniation during thrombosis of the aneurysm, but bioabsorb when they may no longer be needed to inhibit herniation. This can make permanent placement, or release of the device 50, a less consequential procedure as a device 50 comprising bioabsorbable filaments 52 will not remain in the vasculature permanently.

Figure 7B:
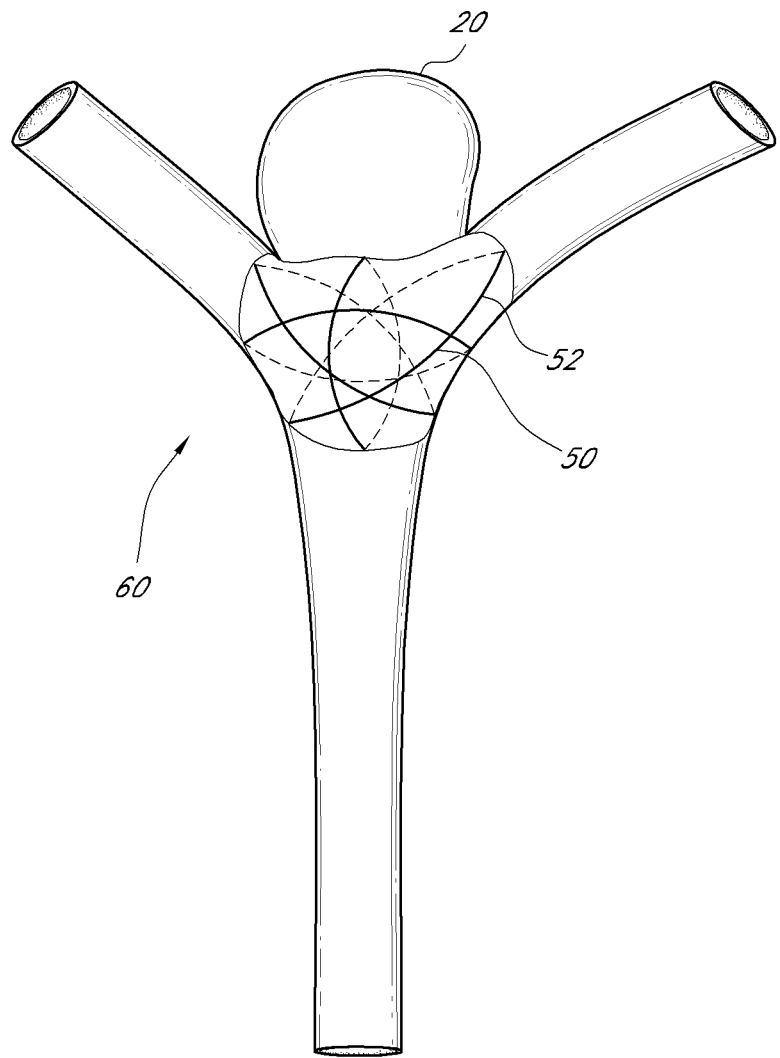
Figure 7C:
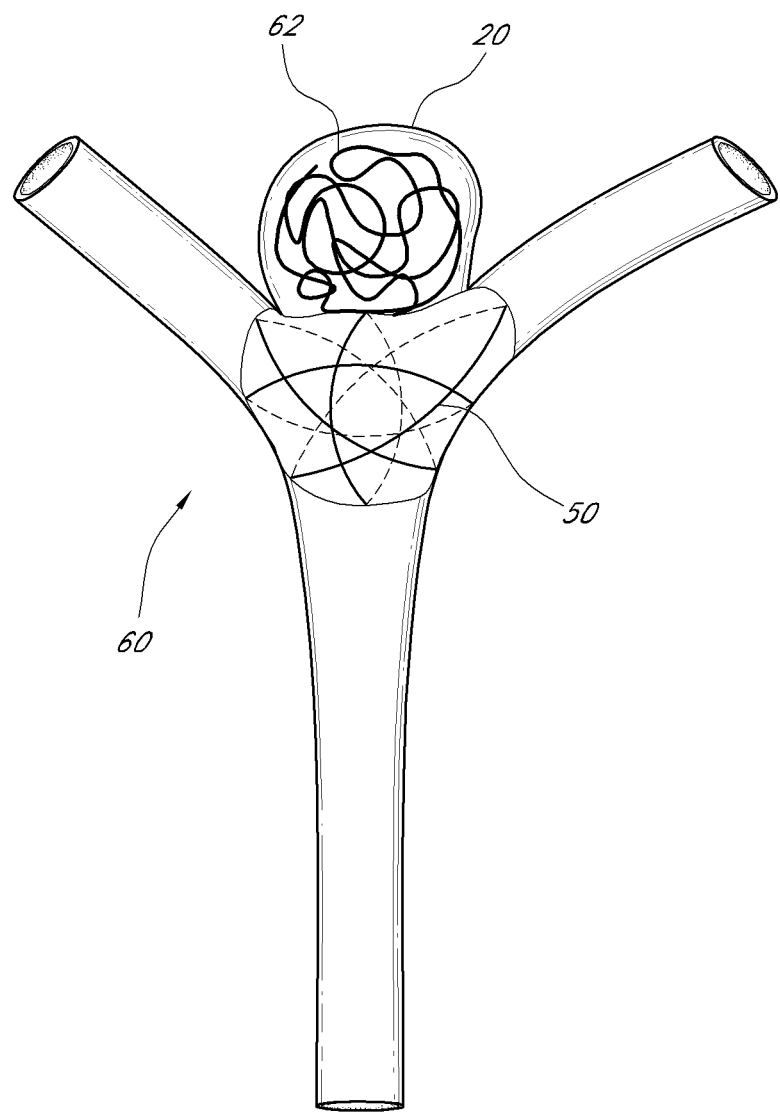

FIGS. 7A-7C illustrate another example embodiment of a method for treating an aneurysm 20 using the device 50. In the method described with respect to FIGS. 6A-6C, the device 50 was pre-assembled outside of the vasculature prior to positioning. By contrast, in the method described with respect to FIGS. 7A-7C, the device 50 is introduced piecemeal and is constructed within the patient at the bifurcation 60. FIG. 7A illustrates a first loop 66 and a second loop 68 positioned across the neck 24 of the aneurysm 20 and the ostia of the afferent and efferent vessels. In some embodiments, the first loop 66 is positioned and the second loop 68 is then positioned inside the first loop 66. In some embodiments, a plane defined by the positioned first loop 66 is substantially perpendicular to the plane of the neck 24 of the aneurysm 20 and a plane defined by the positioned second loop 68 is substantially perpendicular to the plane of the neck 24 of the aneurysm 20. In certain embodiments, the first loop 66 and the second loop 68 are positioned via deployment from a same catheter. In certain embodiments, the first loop 66 is positioned via deployment from a first catheter, the second loop 68 is positioned via deployment from a second catheter, and so on. In some embodiments, the device 50 is not released from a catheter, but each loop 52 is released (e.g., mechanically, electrolytically, etc.) from a catheter. FIG. 7B illustrates the device 50 after it has been fully constructed by positioning additional loops 52. Embolization coils 62 may be inserted in the fundus 22 of the aneurysm 20 prior to construction of the device 50, for example as described above with respect to FIG. 6A, or after construction of the device 50 (e.g., as illustrated in FIG. 7C).

Combinations of methods described herein are also possible. For example, a partially constructed device 50 may be positioned at the junction of the bifurcation 60, and then the device 50 may be fully constructed at the junction of the bifurcation 60. In certain such embodiments, a partially constructed device 50 having some missing loops 52 may allow better access to the aneurysm 20 for easier placement of the embolization coils 62.

Figure 8:
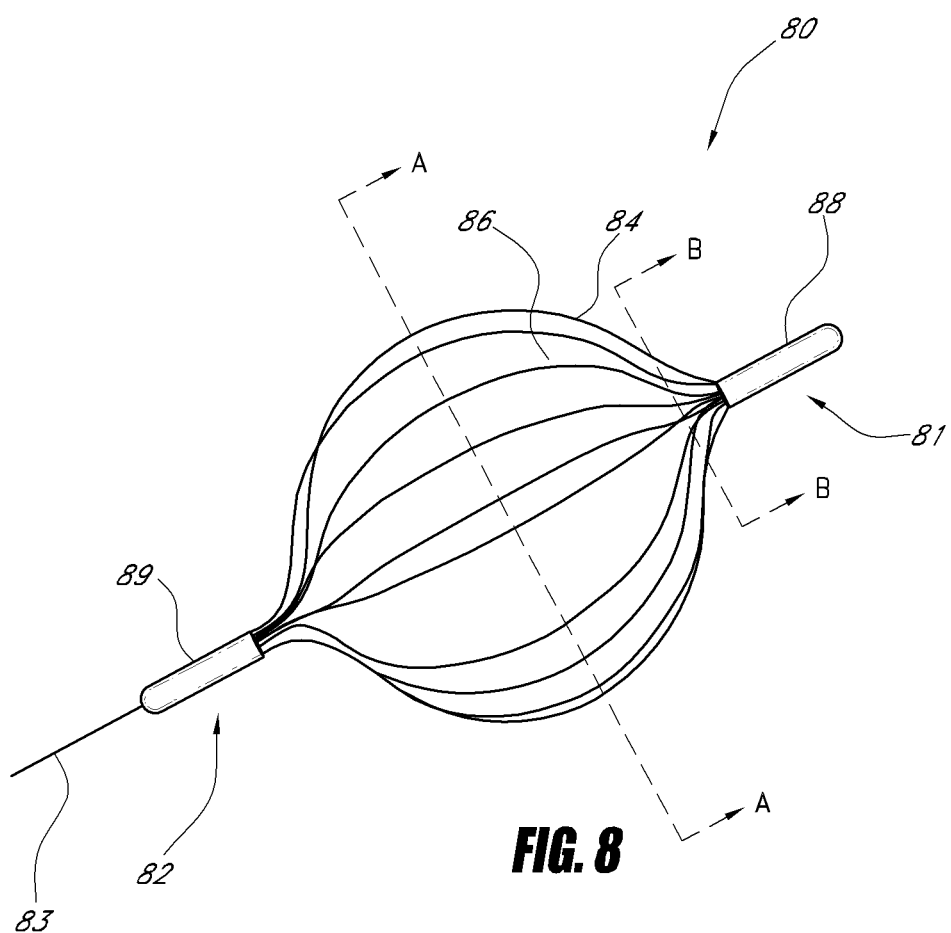
FIG. 8 illustrates another example embodiment of a generally spherical vascular remodeling device.

FIG. 8 illustrates another example embodiment of a generally spherical vascular remodeling device 80. It will be appreciated that the device 80 may be more compliant than the vasculature in which it is deployed such that it may be somewhat misshapen (e.g., non-spherical, for example as illustrated in FIG. 9B) after being deployed, and that the phrase "generally spherical" describes the shape of the device 80 when in an expanded (e.g., fully expanded) state. Additionally, the phrase "generally spherical" distinguishes the device 80, which is generally uniform in each dimension in an expanded state, from tubular stents having a small radial dimension and a large longitudinal dimension in an expanded state. In some embodiments of a generally spherical device, an outer periphery of the device has a shape that deviates by between about 10% and about 25% from an outer periphery of a mathematically perfect sphere. In some embodiments, the device 80 has a length and a width that are within less than about 33% of each other (e.g., having a length of 6 mm and a width of 8 mm, having a length of 6 mm and a width of 8 mm). Embodiments in which the width is greater than the length may be advantageous due to a difference in porosity at a midpoint and an end proximate to an aneurysm. Embodiments in which the length is greater than the width may be advantageous for positioning a portion of the device 80 in a portion of the aneurysm 20 (e.g., to aid in embolization).

The device 80 comprises a first or distal end 81 and a second or proximal end 82 substantially opposite the first end 81. The device 80 further comprises a plurality of filaments 84 extending between the first end 81 and the second end 82. The first end 81 extends outwardly and the second end 82 extends outwardly to form a generally spherical (e.g., oval or oblong) shape similar to a football, a rugby ball, or a watermelon. In certain embodiments, the filaments 84 are coupled at the first end 81 and/or the second end 82 (e.g., by adhering, welding, soldering, combinations thereof, and the like). In the embodiment illustrated in FIG. 8, the device 80 comprises a lead or tail 83, which may be used for releasing and/or retracting the device 80 after deployment, as described herein. In certain embodiments, the device 80 comprises a cut metallic sphere, a single filament, etc.

In certain embodiments, the device 80 is configured to be positioned at a junction of a bifurcation (e.g., a neurovascular bifurcation) comprising at least one afferent vessel, efferent vessels, and an aneurysm having a fundus and a neck. For example, in some embodiments, the device 80 is suitably dimensioned to fit in a junction of a bifurcation (e.g., having a diameter between about 2 mm and about 12 mm, having a diameter between about 6 mm and about 8 mm, having a diameter less than about 12 mm, having a diameter greater than about 2 mm). For another example, in some embodiments, the device 80 is less rigid than a junction of a bifurcation (e.g., due to the number of filaments 84, the material of the filaments 84, the thickness of the filaments 84, the spacing of the filaments 84, the shape of the filaments 84, combinations thereof, and the like). In certain embodiments, the device 80 is configured to act as a scaffolding to inhibit or prevent herniation or prolapse of objects (e.g., embolization coils, thrombi, etc.) out of a neck of an aneurysm. For example, in some embodiments, the filaments 84 are dense enough at the neck of the aneurysm that objects cannot pass. In certain embodiments, the device 80 is configured to permit perfusion of fluid (e.g., blood) to efferent vessels of a bifurcation. For example, in some embodiments, the device 80 is substantially devoid of a covering, mesh, or other material between the filaments 84, thereby allowing fluid to flow substantially unimpeded.

In some embodiments, at least one of the filaments 84 comprises a self-expanding and/or a shape-memory material (e.g., comprising Nitinol, CoCr alloy, etc.), thereby causing the device 80 to be self-expanding under certain conditions (e.g., not restrained by a catheter). In some embodiments, at least one of the filaments 84 comprises a different material than others of the filaments 84 (e.g., some filaments 84 comprising Nitinol and some filaments 84 comprising Nitinol and platinum). In some embodiments, at least one of the filaments 84 comprises a radiopaque material (e.g., platinum). In certain such embodiments, an even number of filaments 84 (e.g., two, four, etc.) comprises a radiopaque material (e.g., platinum). In some embodiments, at least one of the filaments 84 comprises a radiopaque material (e.g., platinum) at least partially wrapped (e.g., coiled) around a self-expanding material (e.g., Nitinol). In some embodiments, at least one of the filaments 84 comprises a self-expanding material with a radiopaque core (e.g., Nitinol with a platinum core) or a radiopaque coating (e.g., Nitinol coated with platinum, tantalum, etc. by physical vapor deposition, chemical vapor deposition, plating, etc.). It will be appreciated that the amount and type of radiopaque material used may depend, inter alia, on price, desired level of radiopacity, mechanical properties of the radiopaque material, and corrosion properties of the radiopaque material. In certain embodiments, the filaments 84 have a substantially circular or ovoid cross section (e.g., embodiments, in which the filaments 84 comprise separate wires). In some embodiments, the filaments 84 have a substantially rectangular or flat cross section (e.g., embodiments, in which the filaments 84 comprise uncut portions of a metallic tube, as described below). Other shapes of filaments 84 and combinations of shapes of filaments 84 are also possible. In certain embodiments, the plurality of filaments 84 comprises between about six and about twelve filaments 84. In certain embodiments, the plurality of filaments 84 comprises at least about six filaments 84, at least about eight filaments 84, or at least about twelve filaments 84. Other numbers of filaments 84 are also possible.

In certain embodiments, at least some of the filaments 84 comprise a polymer. In some embodiments, at least some of the filaments 84 comprise a polymer that is bioabsorbable. In certain embodiments, at least some of the filaments 84 comprise polyglycolic acid (PGA), polylactic acid (PLA), poly (lactic-co-glycolic acid) (PLGA), poly-epsilon-caprolactone (PCL), naturally-derived bioabsorbable polymers (NDB), or combinations thereof (e.g., a first group of the filaments 84 comprising PGA and a second group of the filaments 84 comprising PLA, PLGA, PCL, and/or NDB, a first group of the filaments 84 comprising PLA and a second group of the filaments 84 comprising PGA, PLGA, PCL, and/or NDB, a first group of the filaments 84 comprising PLGA and a second group of the filaments 84 comprising PLA, PGA, PCL, and/or NDB, a first group of the filaments 84 comprising PCL and a second group of the filaments 84 comprising PGA, PLA, PLGA, and/or NDB, a first group of the filaments 84 comprising NDB and a second group of the filaments 84 comprising PGA, PLA, PLGA, and/or PCL, etc.). Other polymers are also possible. PGA, PLA, PLGA, PCL, and NDB are all bioabsorbable; however they have different rates of bioabsorption. The bioabsorption rates of a single polymer can also vary based on, for example, blood characteristics, blood flow, filament 84 dimensions, etc. PLA has the longest bioabsorption rate. In some embodiments, the bioabsorption rate of PLA is at least about ten months. In some embodiments, the bioabsorption rate of PLA is at least about one year. In some embodiments, the bioabsorption rate of PLA is at least about fourteen months. In some embodiments, the bioabsorption rate of PLA is between about 10 months and about 14 months (e.g., about one year). In some embodiments, the bioabsorption rate of PGA is between about 1 week and about 3 weeks. In some embodiments, the bioabsorption rate of PGA is between about 2 weeks and about 4 weeks. The bioabsorption rates of PLGA, PCL, and NDB are generally between the bioabsorption rates of PLA and PGA, and may depend on parameters such as, for example, molecular weight (e.g., generally the higher the molecular weight, the longer the bioabsorption rate), structure (e.g., depending on the arrangement of repeating units), etc. of the polymer. In some embodiments, PLGA, PCL, and NDB may have a bioabsorption rate between about 4 weeks and about 1 year. The bioabsorption rate generally refers to the time lose about 50% of strength. The polymer(s) used in the device 80 may be selected based on the amount of time an aneurysm may take to thrombose (e.g., based on fundus size, neck width, etc.). For example, if an aneurysm is expected to take one month to thrombose and the device 80 is expected to persist through thrombosis but not long thereafter, PGA may be selected. The polymer(s) used in the device 80 may be selected based on the amount of time an aneurysm may take to obliterate (e.g., based on fundus size, neck width, etc.). For example, if an aneurysm is expected to take one year to obliterate and the device 80 is expected to persist through obliteration, PLA may be selected. Other polymers or combinations of polymers can be selected based on the particular aneurysm to be treated and the desired action and/or persistence of the device 80 with respect to the aneurysm. Other selection criteria are also possible. Different combinations of polymers with different rates of bioabsorption can allow for selection of a desired rate of bioabsorption for the device 80. For example, a device 80 with a combination of PGA and PLA filaments 84 may have a rate of bioabsorption in between the rate of bioabsorption of a device 80 comprising only filaments 84 comprising PGA and the rate of bioabsorption of a device 80 comprising only filaments 84 comprising PLA. In some embodiments, the coupling of the filaments 84 may also comprise a bioabsorbable polymer. For example, the filaments 84 may be coupled at the proximal end 82 of the device 80 by intertwining the bioabsorbable filaments 84 or the filaments 84 may be coupled at the proximal end 82 of the device 80 using a separate bioabsorbable component.

The device 80 comprises a plurality of perforations or cells 86 between the filaments 84. In certain embodiments, a percentage of the outer surface of the device 80 covered by the filaments 84 is between about 25% and about 40%. In certain embodiments, a percentage of the outer surface of the device 80 covered by the cells 86 is between about 60% and about 75%. Other porosities are also possible. In some embodiments, porosity distally increases between the second end 82 and an approximate midpoint (e.g., approximately at the line A-A in FIG. 8) and distally decreases between the approximate midpoint and the first end 81. For example, cross-sections taken along the lines A-A and B-B in FIG. 8 each have the same number of filaments 84, but at the cross-section A-A the filaments 84 are spaced further apart from each other than at the cross-section B-B. As an example, if the device comprises ten filaments 84 each having a thickness of 0.5 mm, the porosity at the cross-section A-A would be about 80% with an example circumference of about 25 mm:

$$100\% \times [1-(\approx 0.5 \text{ mm/filament} \times 10 \text{ filaments}/\approx 25 \text{ mm})] \approx 80\%$$

and the porosity at the cross-section B-B would be about 33% with an example circumference of about 7.5 mm:

$$100\% \times [1-(\approx 0.5 \text{ mm/filament} \times 10 \text{ filaments}/\approx 7.5 \text{ mm})] \approx 33\%.$$

High porosity proximate to a midpoint of the device 80 may provide good fluid flow to efferent vessels. Low porosity proximate to the first end 81 of the device 80 may provide good scaffolding properties.

In some embodiments, the device 80 further comprises a radiopaque marker 88 proximate to the first end 81 and/or a radiopaque marker 89 proximate to the second end 82. In certain embodiments, the radiopaque marker 88 may extend at least partially into the aneurysm 20 when the device 80 is positioned at the junction of a bifurcation. In some embodiments, the radiopaque markers 88, 89 may comprise a sleeve positioned or wrapped around the filaments 84, thereby coupling the filaments 84. The radiopaque markers 88, 89 may aid in positioning the device 80 at the junction of a bifurcation.

In some embodiments, the device 80 further comprises a covering (e.g., comprising a porous or non-porous polymer) proximate to the first end 81. In some embodiments, the covering improves the scaffolding properties of the device 80 by reducing the porosity at the first end 81, thereby further inhibiting the herniation or prolapse of embolic material from the aneurysm 20. In certain embodiments, the covering may be attached to the device 80 by sewing the covering from a pre-formed thin film. In certain embodiments, the covering may be mechanically attached (e.g., wrapped around, looped through, etc.) the filaments 84. In certain embodiments, the covering may be deposited (e.g., via physical vapor deposition, chemical vapor deposition, etc.) on the filaments 84. Other portions of the device 80 may also comprise a covering.

Figure 9A:
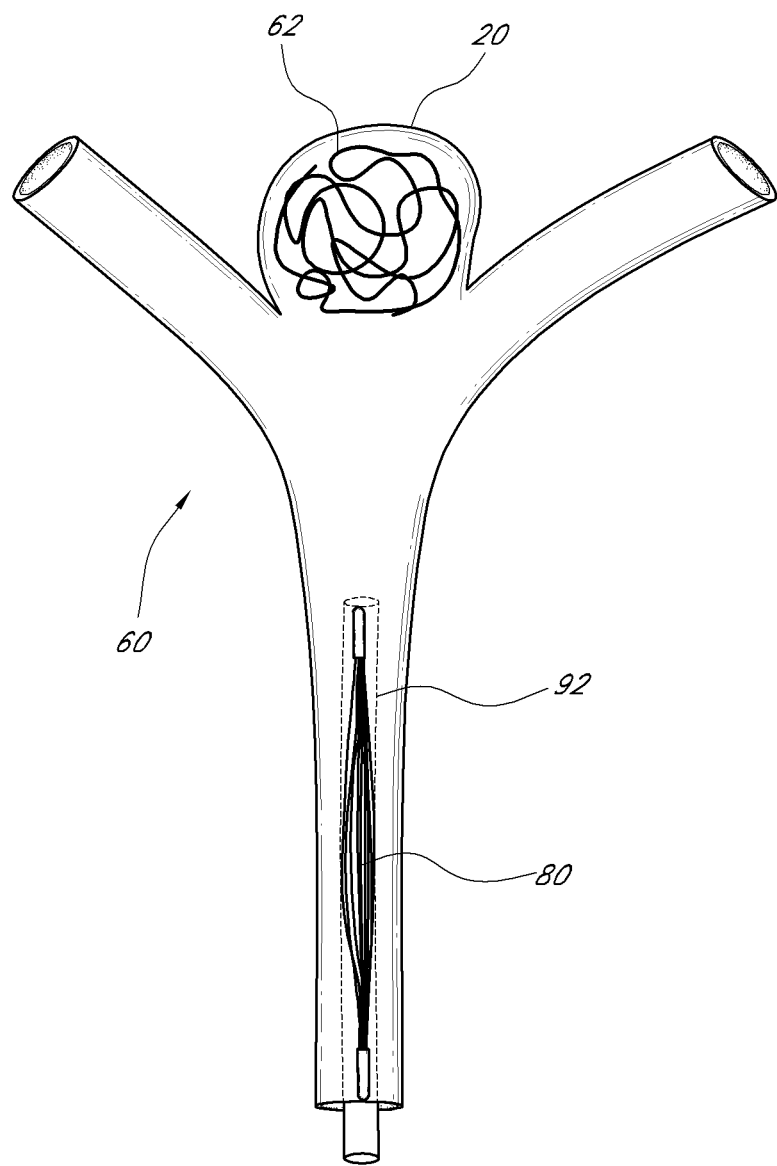
FIGS. 9A-9C illustrate an example embodiment of a method for treating an aneurysm using the device of FIG. 8.
Figure 9B:
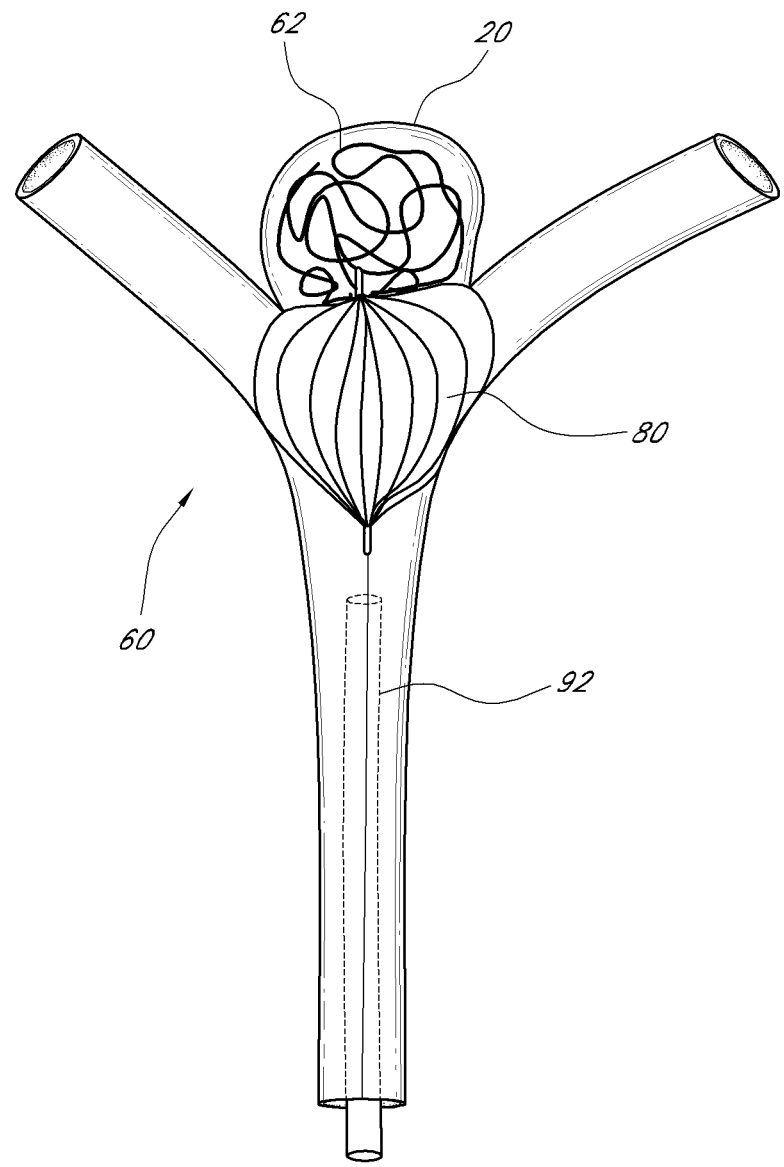
Figure 9C:
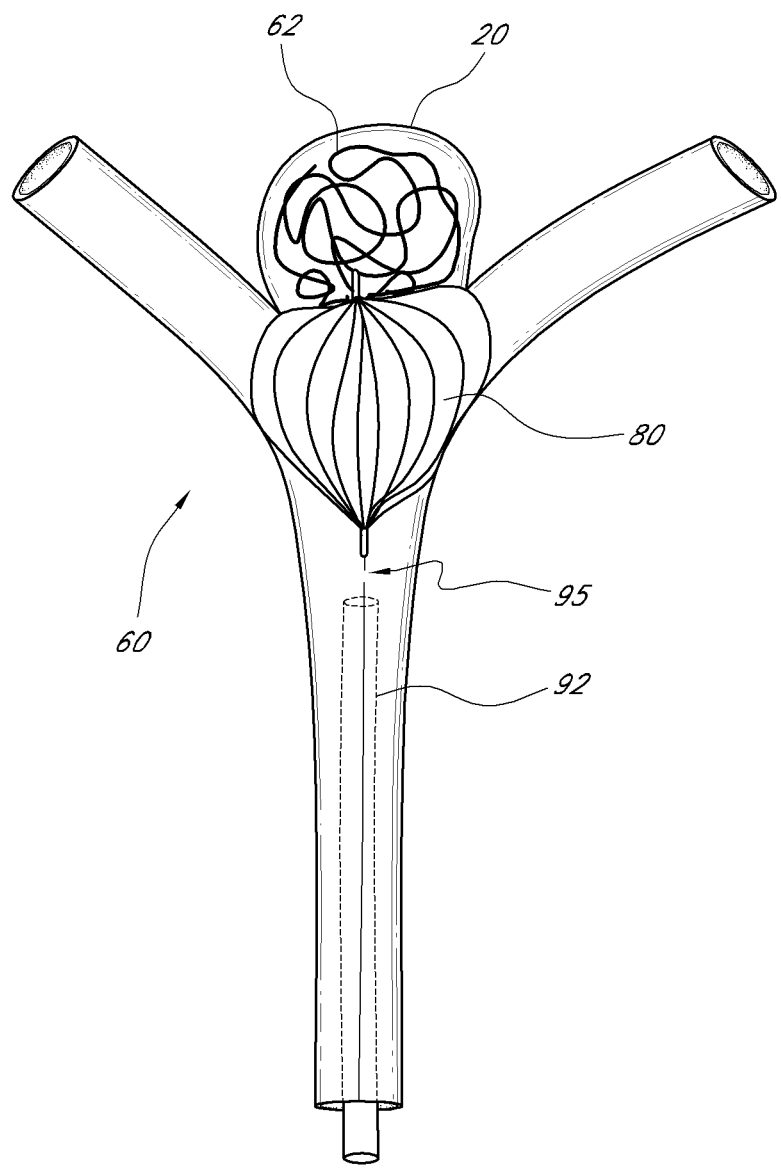

FIGS. 9A-9C illustrate an example embodiment of a method for treating an aneurysm 20 using the device 80. FIG. 9A illustrates a confluence of afferent and efferent vessels or "junction" at a bifurcation 60 having an aneurysm 20. In some embodiments, the vessels are neurovascular or cranial. The aneurysm 20 is illustrated with a plurality of embolization coils 62 having been inserted in the fundus 22 of the aneurysm 20. It will be appreciated that the embolization coils 62 may be a single embolization coil or other embolic material. A catheter 92 (e.g., a microcatheter), at least partially containing a constricted or compressed device 80, is also shown in the afferent vessel. The catheter 92 is small enough and flexible enough to be routed through the vasculature and situated proximate to the aneurysm 20. In some embodiments, the embolization coils 62 are inserted in the fundus 22 of the aneurysm 20 using the catheter 92. In some embodiments, the embolization coils 62 are inserted in the fundus 22 of the aneurysm 20 using a different catheter. In certain such embodiments, a guidewire may be used to guide both catheters.

FIG. 9B illustrates the bifurcation 60 after the device 80 has been deployed from the catheter 92 (e.g., by being pushed out with a plunger, by retracting the catheter 92 while the device 80 remains stationary, etc.). After being deployed from the catheter 92, the device 80 may expand. In some embodiments, the device 80 comprises a self-expanding and/or a shape-memory material that automatically expands towards an uncompressed state or expands towards an uncompressed state upon the application of warm fluid (e.g., saline). The device 80 may substantially conform to the shape of the junction of the bifurcation 60 (e.g., not substantially including portions extending into the afferent and efferent vessels) and locks into place across the ostia of the afferent and efferent vessels and the neck 24 of the aneurysm 20. The device 80 at least partially covers the neck 24 of the aneurysm 20 as well as the afferent and efferent vessels, but does not need to divert flow. The device 80 acts as a scaffolding to inhibit or prevent herniation or prolapse of objects such as the embolization coils 62 and/or thrombi out of the aneurysm 24. The device 80 also allows perfusion of fluid (e.g., blood) from the afferent vessel(s) to the efferent vessel(s).

FIG. 9C illustrates the bifurcation 60 after the device 80 has been released from the catheter 92. In some embodiments, the device 80 is released mechanically (e.g., by a release mechanism). In some embodiments, the device 80 is released electrolytically (e.g., by applying a small current until a portion of the tail 83 proximal to the device 80 corrodes away, as illustrated by the gap 95). The catheter 92 is then withdrawn from the bifurcation 60, thereby leaving or permanently positioning the device 80 at the junction of the bifurcation 60.

It will be appreciated that the term "permanently" does not mean that the device 80 is impossible to remove at a later time. In some embodiments, the device 80 may be retracted into the catheter 92 after being deployed from the catheter 92 (e.g., by pulling on the tail 83). The device 80 may then be deployed, for example at a new angle, at a new rotational position, more proximal or distal to an afferent vessel and/or an efferent vessel, etc. For example, although the device 80 expands towards an uncompressed state after deployment, the resulting shape of the device 80 at the junction of the bifurcation 60 may vary depending on the details of the deployment from the catheter 92 because the device 80 adapts to the shape of the anatomy (e.g., due to the size, shape, number, etc. of the loops 82). Once the user is satisfied with properties of the device 80 (e.g., position, tilt, rotation, shape, interaction with the vessels, etc.), the device 80 may be released as described herein.

In the embodiment illustrated in FIGS. 9A-9C, the embolization coils 62 are inserted in the fundus 22 of the aneurysm 20 before the device 80 has been deployed from the catheter 92 (e.g., using the catheter 92 to insert the embolization coils 62). In the embodiments illustrated in FIGS. 10A-10C, the embolization coils 62 are inserted in the fundus 22 of the aneurysm 20 after the device 80 has been released from the catheter 92 (e.g., using the catheter 92 to insert the embolization coils 62). Combinations are also possible. For example, the embolization coils 62 may be inserted in the fundus 22 of the aneurysm 20 after the device 80 has been deployed from the catheter 92, but prior to the device 80 being released from the catheter 92. For another example, the embolization coils 62 may be inserted into the fundus 22 of the aneurysm 20 after the device 80 has been deployed from the catheter 92 (e.g., in a coil state), and the device 80 may be retracted and redeployed from the catheter 92 (e.g., in a final state).

In certain embodiments, the filaments 84 comprise a bioabsorbable polymer. This bioabsorbability can be advantageous in conjunction with permanent placement of the device 80. For example, after thrombosis of the aneurysm following treatment, the device 80 may no longer be needed to inhibit herniation of material. Certain bioabsorbable embodiments of the device 80 may advantageously inhibit herniation during thrombosis of the aneurysm, but bioabsorb when they may no longer be needed to inhibit herniation. In certain embodiments in which the coupling of the proximal end 82 of the device 80 comprises a bioabsorbable polymer, the coupling may absorb over time, releasing the filaments 84. Once released, the filaments 84 may extend towards and may flatten against the wall of the afferent vessel. This capability may advantageously clear the interior section of the afferent vessel, restoring normal blood flow therein (e.g., in embodiments in which the coupled proximal end may have altered blood flow). In some embodiments, this capability may clear the interior section of the afferent vessel before bioabsorption of the filament 84 is complete. In certain such embodiments, the coupling may comprise a material that bioabsorbs faster than the filaments (e.g., the coupling comprising PGA and the filaments comprising PLA). This can make permanent placement, or release of the device 80, a less consequential procedure as a device 80 comprising bioabsorbable filaments 84 will not remain in the vasculature permanently.

Figure 11:
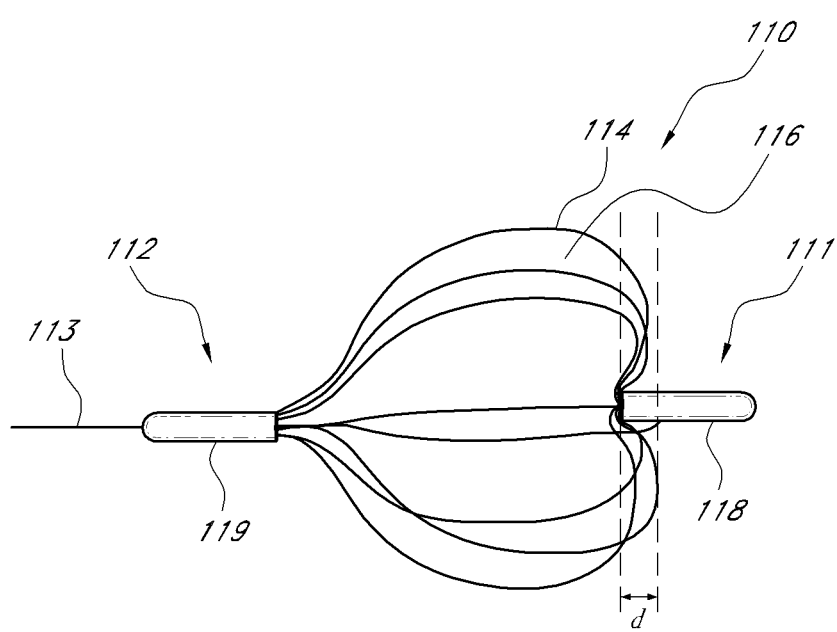
FIG. 11 illustrates yet another example embodiment of a generally spherical vascular remodeling device.
Figure 12:
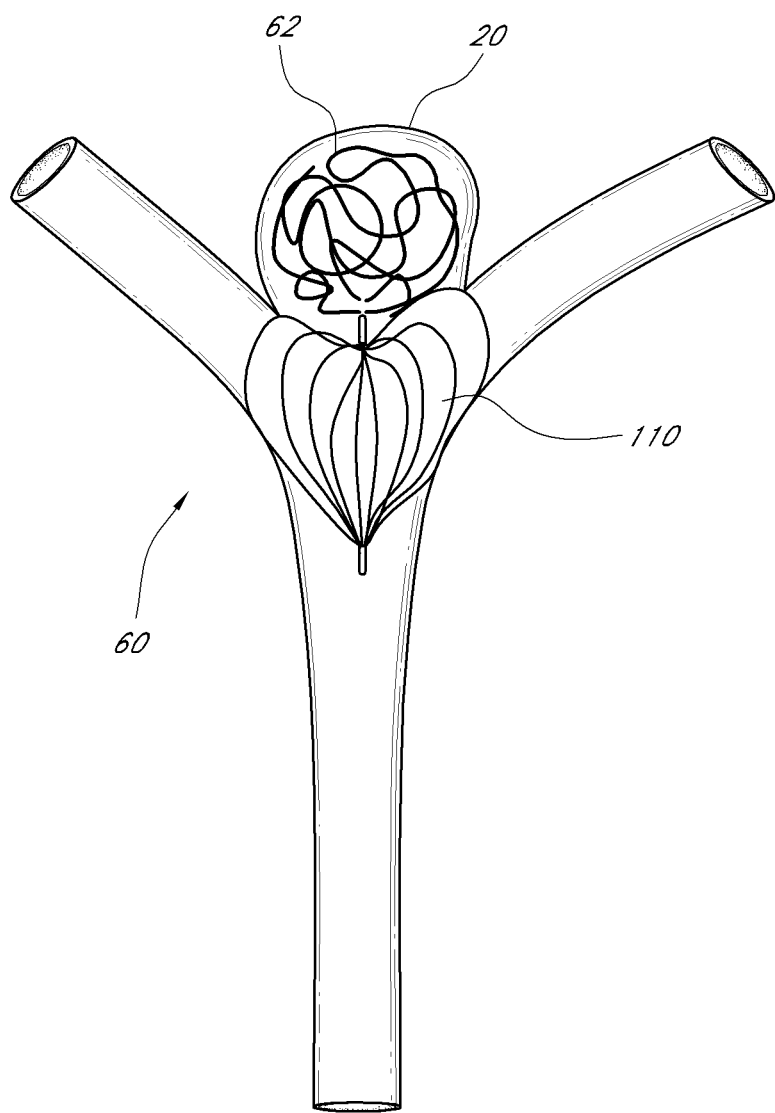
FIG. 12 illustrates an example embodiment of treating an aneurysm using the device of FIG. 11.

FIG. 11 illustrates yet another example embodiment of a generally spherical vascular remodeling device 110. It will be appreciated that the device 110 may be more compliant than the vasculature in which it is deployed such that it may be somewhat misshapen (e.g., non-spherical, for example as illustrated in FIG. 12) after being deployed, and that the phrase "generally spherical" describes the shape of the device 110 when in an expanded (e.g., fully expanded) state. Additionally, the phrase "generally spherical" distinguishes the device 110, which is generally uniform in each dimension in an expanded state, from tubular stents having a small radial dimension and a large longitudinal dimension in an expanded state. In some embodiments of a generally spherical device, an outer periphery of the device has a shape that deviates by between about 10% and about 25% from an outer periphery of a mathematically perfect sphere. In some embodiments, the device 110 has a length and a width that are within less than about 33% of each other (e.g., having a length of 6 mm and a width of 8 mm, having a length of 6 mm and a width of 8 mm). Embodiments in which the width is greater than the length may be advantageous due to a difference in porosity at a midpoint and an end proximate to an aneurysm. Embodiments in which the length is greater than the width may be advantageous for positioning a portion of the device 110 in a portion of the aneurysm 20 (e.g., to aid in embolization).

The device 110 comprises a first or distal end 111 and a second or proximal end 112 substantially opposite the first end 111. The device 110 further comprises a plurality of filaments 114 extending between the first end 111 and the second end 112. In the device 110 illustrated in FIG. 11, the first end 111 extends inwardly and the second end 112 extends outwardly to form a generally spherical shape similar to a pumpkin, a garlic bulb, or a rutabaga. In some embodiments, the filaments 114 are coupled at a position proximal to a bend at a distal end of the device 110 (e.g., as illustrated by the dimension d in FIG. 11). In certain embodiments, the filaments 114 are coupled at the first end 111 and/or the second end 112 (e.g., by adhering, welding, soldering, combinations thereof, and the like). In the embodiment illustrated in FIG. 11, the device 110 comprises a lead or tail 113, which may be used for releasing and/or retracting the device 110 after deployment, as described herein. In certain embodiments, the device 110 comprises a cut metallic sphere, a single filament, etc. It will be appreciated that a device in which the first end extends outwardly and the second end extends inwardly and a device in which the first end extends inwardly and the second end extends inwardly are also possible.

In certain embodiments, the device 110 is configured to be positioned at a junction of a bifurcation (e.g., a neurovascular bifurcation) comprising at least one afferent vessel, efferent vessels, and an aneurysm having a fundus and a neck. For example, in some embodiments, the device 110 is suitably dimensioned to fit in a junction of a bifurcation (e.g., having a diameter between about 2 mm and about 12 mm, having a diameter between about 6 mm and about 8 mm, having a diameter less than about 12 mm, having a diameter greater than about 2 mm). For another example, in some embodiments, the device 110 is less rigid than a junction of a bifurcation (e.g., due to the number of filaments 114, the material of the filaments 114, the thickness of the filaments 114, the spacing of the filaments 114, the shape of the filaments 114, combinations thereof, and the like). In certain embodiments, the device 110 is configured to act as a scaffolding to inhibit or prevent herniation or prolapse of objects (e.g., embolization coils, thrombi, etc.) out of a neck of an aneurysm. For example, in some embodiments, the filaments 114 are dense enough at the neck of the aneurysm that objects cannot pass. In certain embodiments, the device 110 is configured to permit perfusion of fluid (e.g., blood) to efferent vessels of a bifurcation. For example, in some embodiments, the device 110 is substantially devoid of a covering, mesh, or other material between the filaments 114, thereby allowing fluid to flow substantially unimpeded.

In some embodiments, at least one of the filaments 114 comprises a self-expanding and/or a shape-memory material (e.g., comprising Nitinol, CoCr alloy, etc.), thereby causing the device 110 to be self-expanding under certain conditions (e.g., not restrained by a catheter). In some embodiments, at least one of the filaments 114 comprises a different material than others of the filaments 114 (e.g., some filaments 114 comprising Nitinol and some filaments 114 comprising Nitinol and platinum). In some embodiments, at least one of the filaments 114 comprises a radiopaque material (e.g., platinum). In certain such embodiments, an even number of filaments 84 (e.g., two, four, etc.) comprises a radiopaque material (e.g., platinum). In some embodiments, at least one of the filaments 84 comprises a radiopaque material (e.g., platinum) at least partially wrapped (e.g., coiled) around a self-expanding material (e.g., Nitinol). In some embodiments, at least one of the filaments 84 comprises a self-expanding material with a radiopaque core (e.g., Nitinol with a platinum core) or a radiopaque coating (e.g., Nitinol coated with platinum, tantalum, etc. by physical vapor deposition, chemical vapor deposition, plating, etc.). It will be appreciated that the amount and type of radiopaque material used may depend, inter alia, on price, desired level of radiopacity, mechanical properties of the radiopaque material, and corrosion properties of the radiopaque material. In certain embodiments, the filaments 114 have a substantially circular or ovoid cross section (e.g., embodiments, in which the filaments 84 comprise separate wires). In some embodiments, the filaments 114 have a substantially rectangular or flat cross section (e.g., embodiments, in which the filaments 84 comprise uncut portions of a metallic tube). Other shapes of filaments 114 and combinations of shapes of filaments 114 are also possible. In certain embodiments, the plurality of filaments 84 comprises between about six and about twelve filaments 114. In certain embodiments, the plurality of filaments 114 comprises at least about six filaments 114, at least about eight filaments 114, or at least about twelve filaments 114. Other numbers of filaments 114 are also possible.

In certain embodiments, at least some of the filaments 114 comprise a polymer. In some embodiments, at least some of the filaments 114 comprise a polymer that is bioabsorbable. In certain embodiments, at least some of the filaments 114 comprise polyglycolic acid (PGA), polylactic acid (PLA), poly(lactic-co-glycolic acid) (PLGA), poly-epsilon-caprolactone (PCL), naturally-derived bioabsorbable polymers (NDB), or combinations thereof (e.g., a first group of the filaments 114 comprising PGA and a second group of the filaments 114 comprising PLA, PLGA, PCL, and/or NDB, a first group of the filaments 114 comprising PLA and a second group of the filaments 114 comprising PGA, PLGA, PCL, and/or NDB, a first group of the filaments 114 comprising PLGA and a second group of the filaments 114 comprising PLA, PGA, PCL, and/or NDB, a first group of the filaments 114 comprising PCL and a second group of the filaments 114 comprising PGA, PLA, PLGA, and/or NDB, a first group of the filaments 114 comprising NDB and a second group of the filaments 114 comprising PGA, PLA, PLGA, and/or PCL, etc.). Other polymers are also possible. PGA, PLA, PLGA, PCL, and NDB are all bioabsorbable; however they have different rates of bioabsorption. The bioabsorption rates of a single polymer can also vary based on, for example, blood characteristics, blood flow, filament 114 dimensions, etc. PLA has the longest bioabsorption rate. In some embodiments, the bioabsorption rate of PLA is at least about ten months. In some embodiments, the bioabsorption rate of PLA is at least about one year. In some embodiments, the bioabsorption rate of PLA is at least about fourteen months. In some embodiments, the bioabsorption rate of PLA is between about 10 months and about 14 months (e.g., about one year). In some embodiments, the bioabsorption rate of PGA is between about 1 week and about 3 weeks. In some embodiments, the bioabsorption rate of PGA is between about 2 weeks and about 4 weeks. The bioabsorption rates of PLGA, PCL, and NDB are generally between the bioabsorption rates of PLA and PGA, and may depend on parameters such as, for example, molecular weight (e.g., generally the higher the molecular weight, the longer the bioabsorption rate), structure (e.g., depending on the arrangement of repeating units), etc. of the polymer. In some embodiments, PLGA, PCL, and NDB may have a bioabsorption rate between about 4 weeks and about 1 year. The bioabsorption rate generally refers to the time lose about 50% of strength. The polymer(s) used in the device 110 may be selected based on the amount of time an aneurysm may take to thrombose (e.g., based on fundus size, neck width, etc.). For example, if an aneurysm is expected to take one month to thrombose and the device 110 is expected to persist through thrombosis but not long thereafter, PGA may be selected. The polymer(s) used in the device 110 may be selected based on the amount of time an aneurysm may take to obliterate (e.g., based on fundus size, neck width, etc.). For example, if an aneurysm is expected to take one year to obliterate and the device 110 is expected to persist through obliteration, PLA may be selected. Other polymers or combinations of polymers can be selected based on the particular aneurysm to be treated and the desired action and/or persistence of the device 110 with respect to the aneurysm. Other selection criteria are also possible. Different combinations of polymers with different rates of bioabsorption can allow for selection of a desired rate of bioabsorption for the device 110. For example, a device 110 with a combination of PGA and PLA filaments 114 may have a rate of bioabsorption in between the rate of bioabsorption of a device 110 comprising only filaments 114 comprising PGA and the rate of bioabsorption of a device 110 comprising only filaments 114 comprising PLA. In some embodiments, the coupling of the filaments 114 may also comprise a bioabsorbable polymer. For example, the filaments 114 may be coupled at the proximal end 112 of the device 110 by intertwining the bioabsorbable filaments 114 or the filaments 114 may be coupled at the proximal end 112 of the device 110 using a separate bioabsorbable component.

As described herein, certain embodiments comprising bioabsorbable filaments (e.g., the filaments 114) can be advantageous in conjunction with permanent placement of the device (e.g., the device 110). In certain embodiments in which the coupling of the proximal end 112 of the device 110 comprises a bioabsorbable polymer, the coupling may absorb over time, releasing the filaments 114. Once released, the filaments 114 may extend towards and may flatten against the wall of the afferent vessel. This capability may advantageously clear the interior section of the afferent vessel, restoring normal blood flow therein (e.g., in embodiments in which the coupled proximal end may have altered blood flow). In some embodiments, this capability may clear the interior section of the afferent vessel before bioabsorption of the filament 114 is complete. In certain such embodiments, the coupling may comprise a material that bioabsorbs faster than the filaments (e.g., the coupling comprising PGA and the filaments comprising PLA).

The device 110 comprises a plurality of perforations or cells 116 between the filaments 114. In certain embodiments, a percentage of the outer surface of the device 110 covered by the filaments 114 is between about 25% and about 40%. In certain embodiments, a percentage of the outer surface of the device 110 covered by the cells 116 is between about 60% and about 75%. Other porosities are also possible. In some embodiments, porosity distally increases between the second end 112 and an approximate midpoint and distally decreases between the approximate midpoint and the first end 111.

In some embodiments, the device 110 further comprises a radiopaque marker 118 proximate to the first end 111 and/or a radiopaque marker 119 proximate to the second end 112. In certain embodiments, the radiopaque marker 118 may extend at least partially into the aneurysm 20 when the device 110 is positioned at the junction of a bifurcation. In some embodiments, the radiopaque markers 118, 119 may comprise a sleeve situated or wrapped around the filaments 114, thereby coupling the filaments 114. The radiopaque markers 118, 119 may aid in positioning the device 110 at the junction of a bifurcation.

In some embodiments, the device 110 further comprises a covering (e.g., comprising a porous or non-porous polymer) proximate to the first end 111. In some embodiments, the covering improves the scaffolding properties of the device 110 by reducing the porosity at the first end 111, thereby further inhibiting the herniation or prolapse of embolic material from the aneurysm 20. In certain embodiments, the covering may be attached to the device 110 by sewing the covering from a pre-formed thin film. In certain embodiments, the covering may be mechanically attached (e.g., wrapped around, looped through, etc.) the filaments 114. In certain embodiments, the covering may be deposited (e.g., via physical vapor deposition, chemical vapor deposition, etc.) on the filaments 114. Other portions of the device 110 may also comprise a covering.

FIG. 12 illustrates an example embodiment of treating an aneurysm 20 using the device 110. The junction at the bifurcation 60, including the treated aneurysm 20, illustrated in FIG. 12 may be the result of performing a method similar to the method described with respect to FIGS. 9A-9C, the result of performing a method similar to the method described with respect to FIGS. 10A-10C, combinations thereof, and the like.

As described above, the term "bifurcation" described herein is not limited to the particular vasculature illustrated in FIGS. 6A-7C, 9A-10C, and 12, for example having efferent vessels at substantially different angles, having efferent vessels that are substantially different sizes, and/or having a different quantity of efferent vessels and/or the aneurysm of the bifurcation may be offset with respect to the junction (e.g., having a neck substantially open to one efferent vessel), tilted with respect to a plane created by the vessels (e.g., into or out of the page), etc.

Figure 13:
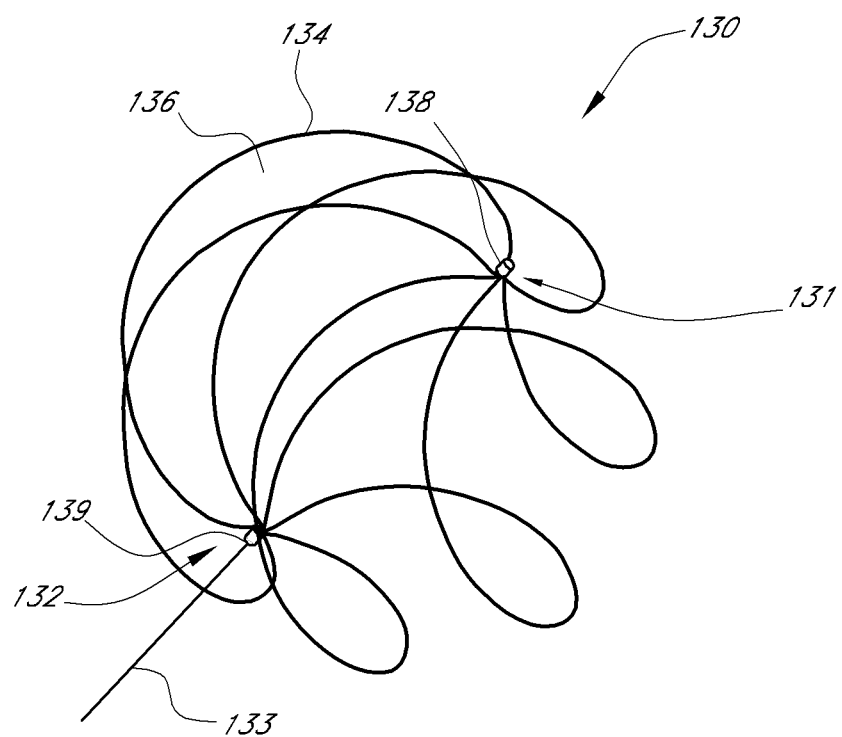
FIG. 13 illustrates still another example embodiment of a generally spherical vascular remodeling device.

FIG. 13 illustrates still another example embodiment of a generally spherical vascular remodeling device 130. It will be appreciated that the device 130 may be more compliant than the vasculature in which it is deployed such that it may be somewhat misshapen (e.g., non-spherical) after being deployed, and that the phrase "generally spherical" describes the shape of the device 130 when in an expanded (e.g., fully expanded) state. Additionally, the phrase "generally spherical" distinguishes the device 130, which is generally uniform in each dimension in an expanded state, from tubular stents having a small radial dimension and a large longitudinal dimension in an expanded state. In some embodiments of a generally spherical device, an outer periphery of the device has a shape that deviates by between about 10% and about 25% from an outer periphery of a mathematically perfect sphere. In some embodiments, the device 130 has a length and a width that are within less than about 33% of each other (e.g., having a length of 6 mm and a width of 8 mm, having a length of 6 mm and a width of 8 mm). Embodiments in which the width is greater than the length may be advantageous due to a difference in porosity at a midpoint and an end proximate to an aneurysm. Embodiments in which the length is greater than the width may be advantageous for positioning a portion of the device 130 in a portion of the aneurysm 20 (e.g., to aid in embolization).

The device 130 comprises a first or distal end 131 and a second or proximal end 132 substantially opposite the first end 131. The device 130 further comprises a plurality of filaments 134 extending between the first end 131 and the second end 132. In the device 130 illustrated in FIG. 13, the first end 131 extends outwardly and the second end 132 extends outwardly to form a generally spherical shape similar to a twisted sphere (e.g., after rotating one or both ends 81, 82 of the device 80 illustrated in FIG. 8 with respect to each other). In certain embodiments, the filaments 134 are coupled at the first end 131 and/or the second end 132 (e.g., by adhering, welding, soldering, combinations thereof, and the like). In contrast to the filaments 84 of the device 80 illustrated in FIG. 8, which in some embodiments are straight enough to form a plane, the filaments 134 of the device 130 are longitudinally angled at or adjacent to at least the second end 132. In the embodiment illustrated in FIG. 13, the device 130 comprises a lead or tail 133, which may be used for releasing and/or retracting the device 130 after deployment, as described herein. In some embodiments, deployment and/or retraction of the device 130 uses less force than retraction of, for example, the devices 50, 80, 110. In certain embodiments, the device 130 comprises a cut metallic sphere, a single filament, etc.

In certain embodiments, the device 130 is configured to be positioned at a junction of a bifurcation (e.g., a neurovascular bifurcation) comprising at least one afferent vessel, efferent vessels, and an aneurysm having a fundus and a neck. For example, in some embodiments, the device 130 is suitably dimensioned to fit in a junction of a bifurcation (e.g., having a diameter between about 2 mm and about 12 mm, having a diameter between about 6 mm and about 8 mm, having a diameter less than about 12 mm, having a diameter greater than about 2 mm). For another example, in some embodiments, the device 130 is less rigid than a junction of a bifurcation (e.g., due to the number of filaments 134, the material of the filaments 134, the thickness of the filaments 134, the spacing of the filaments 134, the shape of the filaments 134, combinations thereof, and the like). In certain embodiments, the device 130 is configured to act as a scaffolding to inhibit or prevent herniation or prolapse of objects (e.g., embolization coils, thrombi, etc.) out of a neck of an aneurysm. For example, in some embodiments, the filaments 134 are dense enough at the neck of the aneurysm that objects cannot pass. In certain embodiments, the device 130 is configured to permit perfusion of fluid (e.g., blood) to efferent vessels of a bifurcation. For example, in some embodiments, the device 130 is substantially devoid of a covering, mesh, or other material between the filaments 134, thereby allowing fluid to flow substantially unimpeded.

In some embodiments, at least one of the filaments 134 comprises a self-expanding and/or a shape-memory material (e.g., comprising Nitinol, CoCr alloy, etc.), thereby causing the device 130 to be self-expanding under certain conditions (e.g., not restrained by a catheter). In some embodiments, at least one of the filaments 134 comprises a different material than others of the filaments 134 (e.g., some filaments 134 comprising Nitinol and some filaments 134 comprising Nitinol and platinum). In some embodiments, at least one of the filaments 134 comprises a radiopaque material (e.g., platinum). In certain such embodiments, an even number of filaments 84 (e.g., two, four, etc.) comprises a radiopaque material (e.g., platinum). In some embodiments, at least one of the filaments 84 comprises a radiopaque material (e.g., platinum) at least partially wrapped (e.g., coiled) around a self-expanding material (e.g., Nitinol). In some embodiments, at least one of the filaments 84 comprises a self-expanding material with a radiopaque core (e.g., Nitinol with a platinum core) or a radiopaque coating (e.g., Nitinol coated with platinum, tantalum, etc. by physical vapor deposition, chemical vapor deposition, plating, etc.). It will be appreciated that the amount and type of radiopaque material used may depend, inter alia, on price, desired level of radiopacity, mechanical properties of the radiopaque material, and corrosion properties of the radiopaque material. In certain embodiments, the filaments 134 have a substantially circular or ovoid cross section (e.g., embodiments, in which the filaments 84 comprise separate wires). In some embodiments, the filaments 134 have a substantially rectangular or flat cross section (e.g., embodiments, in which the filaments 84 comprise uncut portions of a metallic tube). Other shapes of filaments 134 and combinations of shapes of filaments 134 are also possible. In certain embodiments, the plurality of filaments 84 comprises between about six and about twelve filaments 134. In certain embodiments, the plurality of filaments 134 comprises at least about six filaments 134, at least about eight filaments 134, or at least about twelve filaments 134. Other numbers of filaments 134 are also possible.

In certain embodiments, at least some of the filaments 134 comprise a polymer. In some embodiments, at least some of the filaments 134 comprise a polymer that is bioabsorbable. In certain embodiments, at least some of the filaments 134 comprise polyglycolic acid (PGA), polylactic acid (PLA), poly(lactic-co-glycolic acid) (PLGA), poly-epsilon-caprolactone (PCL), naturally-derived bioabsorbable polymers (NDB), or combinations thereof (e.g., a first group of the filaments 134 comprising PGA and a second group of the filaments 134 comprising PLA, PLGA, PCL, and/or NDB, a first group of the filaments 134 comprising PLA and a second group of the filaments 134 comprising PGA, PLGA, PCL, and/or NDB, a first group of the filaments 134 comprising PLGA and a second group of the filaments 134 comprising PLA, PGA, PCL, and/or NDB, a first group of the filaments 134 comprising PCL and a second group of the filaments 134 comprising PGA, PLA, PLGA, and/or NDB, a first group of the filaments 134 comprising NDB and a second group of the filaments 134 comprising PGA, PLA, PLGA, and/or PCL, etc.). Other polymers are also possible. PGA, PLA, PLGA, PCL, and NDB are all bioabsorbable; however they have different rates of bioabsorption. The bioabsorption rates of a single polymer can also vary based on, for example, blood characteristics, blood flow, filament 134 dimensions, etc. PLA has the longest bioabsorption rate. In some embodiments, the bioabsorption rate of PLA is at least about ten months. In some embodiments, the bioabsorption rate of PLA is at least about one year. In some embodiments, the bioabsorption rate of PLA is at least about fourteen months. In some embodiments, the bioabsorption rate of PLA is between about 10 months and about 14 months (e.g., about one year). In some embodiments, the bioabsorption rate of PGA is between about 1 week and about 3 weeks. In some embodiments, the bioabsorption rate of PGA is between about 2 weeks and about 4 weeks. The bioabsorption rates of PLGA, PCL, and NDB are generally between the bioabsorption rates of PLA and PGA, and may depend on parameters such as, for example, molecular weight (e.g., generally the higher the molecular weight, the longer the bioabsorption rate), structure (e.g., depending on the arrangement of repeating units), etc. of the polymer. In some embodiments, PLGA, PCL, and NDB may have a bioabsorption rate between about 4 weeks and about 1 year. The bioabsorption rate generally refers to the time lose about 50% of strength. The polymer(s) used in the device 130 may be selected based on the amount of time an aneurysm may take to thrombose (e.g., based on fundus size, neck width, etc.). For example, if an aneurysm is expected to take one month to thrombose and the device 130 is expected to persist through thrombosis but not long thereafter, PGA may be selected. The polymer(s) used in the device 130 may be selected based on the amount of time an aneurysm may take to obliterate (e.g., based on fundus size, neck width, etc.). For example, if an aneurysm is expected to take one year to obliterate and the device 130 is expected to persist through obliteration, PLA may be selected. Other polymers or combinations of polymers can be selected based on the particular aneurysm to be treated and the desired action and/or persistence of the device 130 with respect to the aneurysm. Other selection criteria are also possible. Different combinations of polymers with different rates of bioabsorption can allow for selection of a desired rate of bioabsorption for the device 130. For example, a device 130 with a combination of PGA and PLA filaments 134 may have a rate of bioabsorption in between the rate of bioabsorption of a device 130 comprising only filaments 134 comprising PGA and the rate of bioabsorption of a device 130 comprising only filaments 134 comprising PLA. In some embodiments, the coupling of the filaments 134 may also comprise a bioabsorbable polymer. For example, the filaments 134 may be coupled at the proximal end 132 of the device 130 by intertwining the bioabsorbable filaments 134 or the filaments 134 may be coupled at the proximal end 132 of the device 130 using a separate bioabsorbable component.

As described herein, certain embodiments comprising bioabsorbable filaments (e.g., the filaments 134) can be advantageous in conjunction with permanent placement of the device (e.g., the device 130). In certain embodiments in which the coupling of the proximal end 132 of the device 130 comprises a bioabsorbable polymer, the coupling may absorb over time, releasing the filaments 134. Once released, the filaments 134 may extend towards and may flatten against the wall of the afferent vessel. This capability may advantageously clear the interior section of the afferent vessel, restoring normal blood flow therein (e.g., in embodiments in which the coupled proximal end may have altered blood flow). In some embodiments, this capability may clear the interior section of the afferent vessel before bioabsorption of the filament 134 is complete. In certain such embodiments, the coupling may comprise a material that bioabsorbs faster than the filaments (e.g., the coupling comprising PGA and the filaments comprising PLA).

The device 130 comprises a plurality of perforations or cells 136 between the filaments 134. In certain embodiments, a percentage of the outer surface of the device 130 covered by the filaments 134 is between about 25% and about 40%. In certain embodiments, a percentage of the outer surface of the device 130 covered by the cells 136 is between about 60% and about 75%. Other porosities are also possible. In some embodiments, porosity distally increases between the second end 132 and an approximate midpoint and distally decreases between the approximate midpoint and the first end 131.

In some embodiments, the device 130 further comprises a radiopaque marker 138 proximate to the first end 131 and/or a radiopaque marker 139 proximate to the second end 132. In certain embodiments, the radiopaque marker 138 may extend at least partially into the aneurysm 20 when the device 130 is positioned at the junction of a bifurcation. In some embodiments, the radiopaque markers 138, 139 may comprise a sleeve situated or wrapped around the filaments 134, thereby coupling the filaments 134. The radiopaque markers 138, 139 may aid in positioning the device 130 at the junction of a bifurcation.

In some embodiments, the device 130 further comprises a covering (e.g., comprising a porous or non-porous polymer) proximate to the first end 131. In some embodiments, the covering improves the scaffolding properties of the device 130 by reducing the porosity at the first end 131, thereby further inhibiting the herniation or prolapse of embolic material from the aneurysm 20. In certain embodiments, the covering may be attached to the device 130 by sewing the covering from a pre-formed thin film. In certain embodiments, the covering may be mechanically attached (e.g., wrapped around, looped through, etc.) the filaments 134. In certain embodiments, the covering may be deposited (e.g., via physical vapor deposition, chemical vapor deposition, etc.) on the filaments 134. Other portions of the device 130 may also comprise a covering.

Figure 10A:
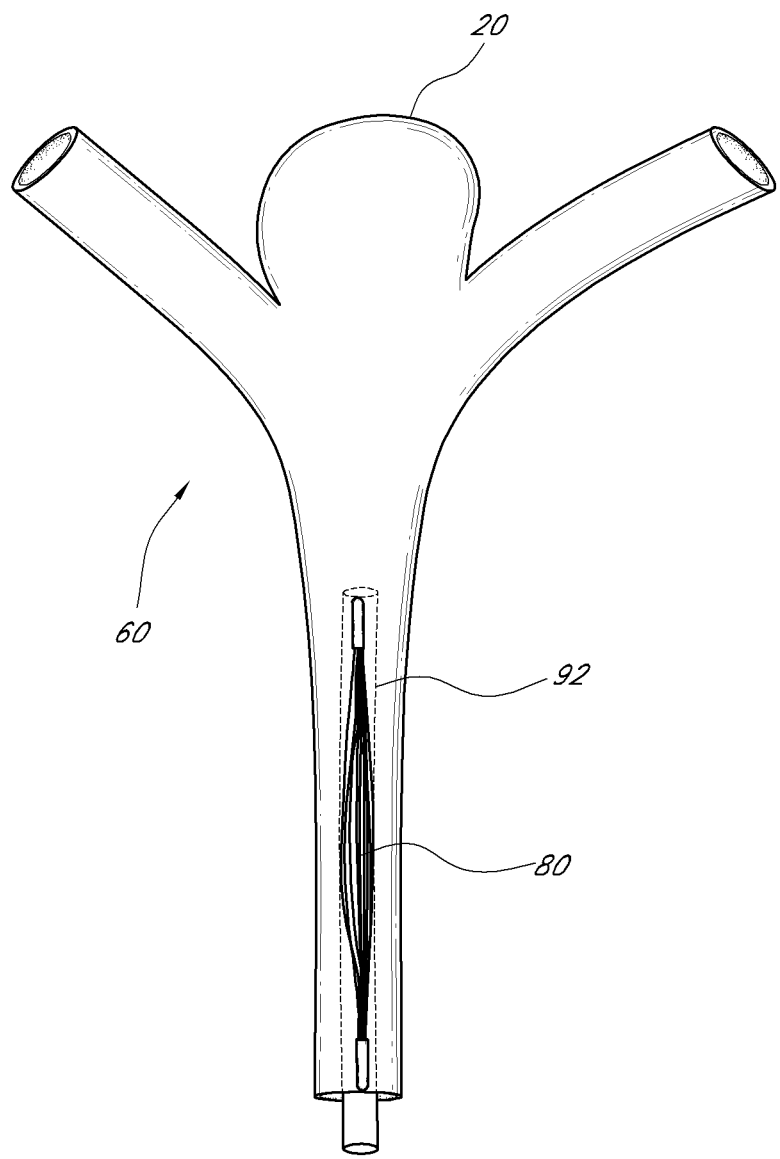
FIGS. 10A-10C illustrate another example embodiment of a method for treating an aneurysm using the device of FIG. 8.
Figure 10B:
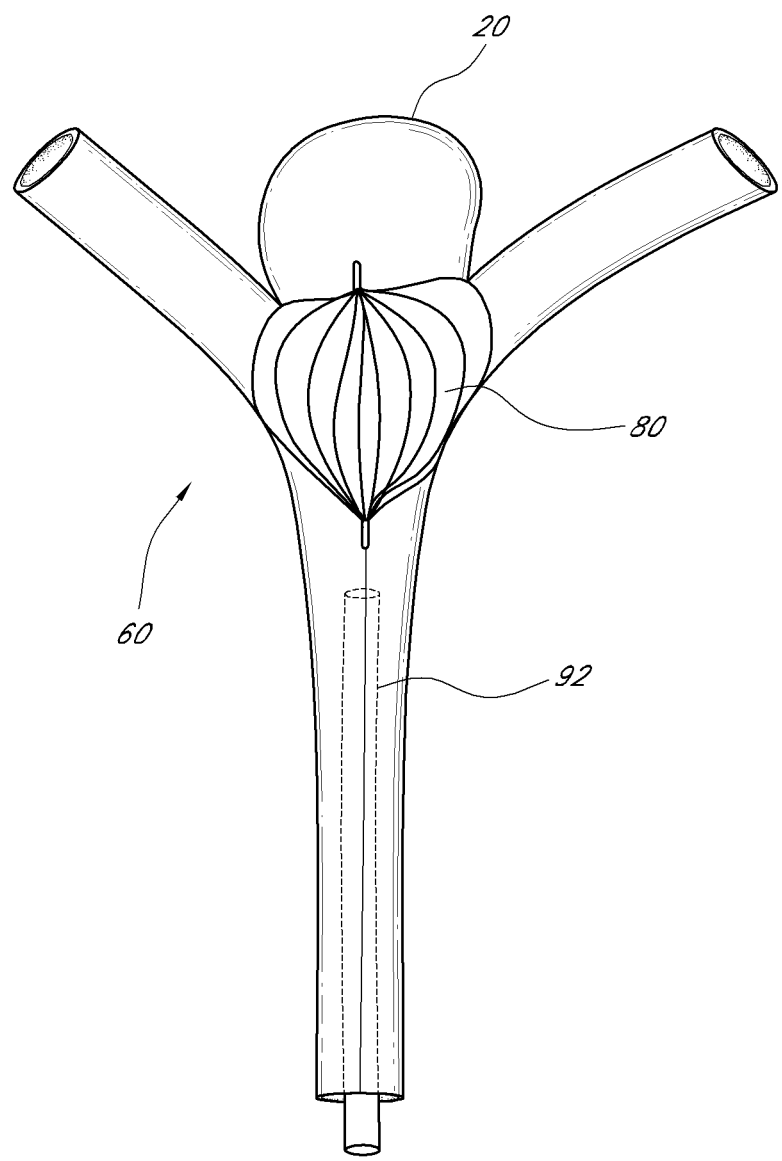
Figure 10C:
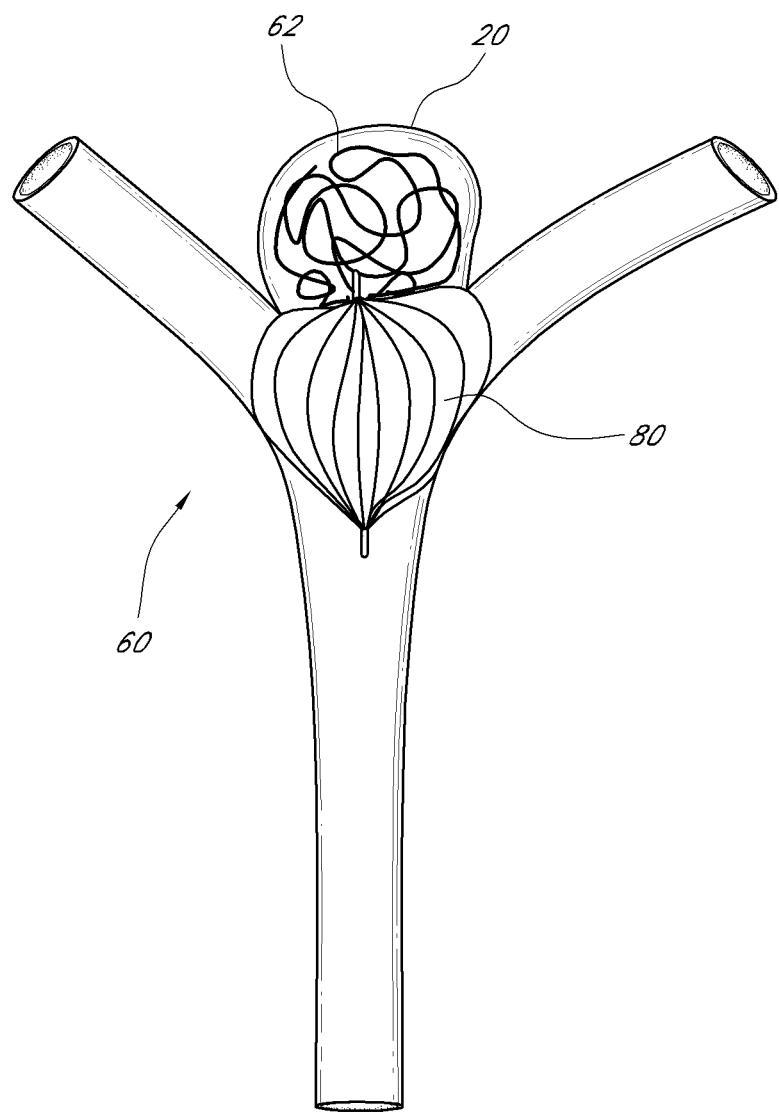

The device 130 may be positioned and retracted as described, for example, by performing a method similar to the method described with respect to FIGS. 9A-9C, by performing a method similar to the method described with respect to FIGS. 10A-10C, combinations thereof, and the like. As described above, the device 130 may be particularly advantageous for embodiments in which retraction and redeployment of the device 130 is likely.

Figure 14:
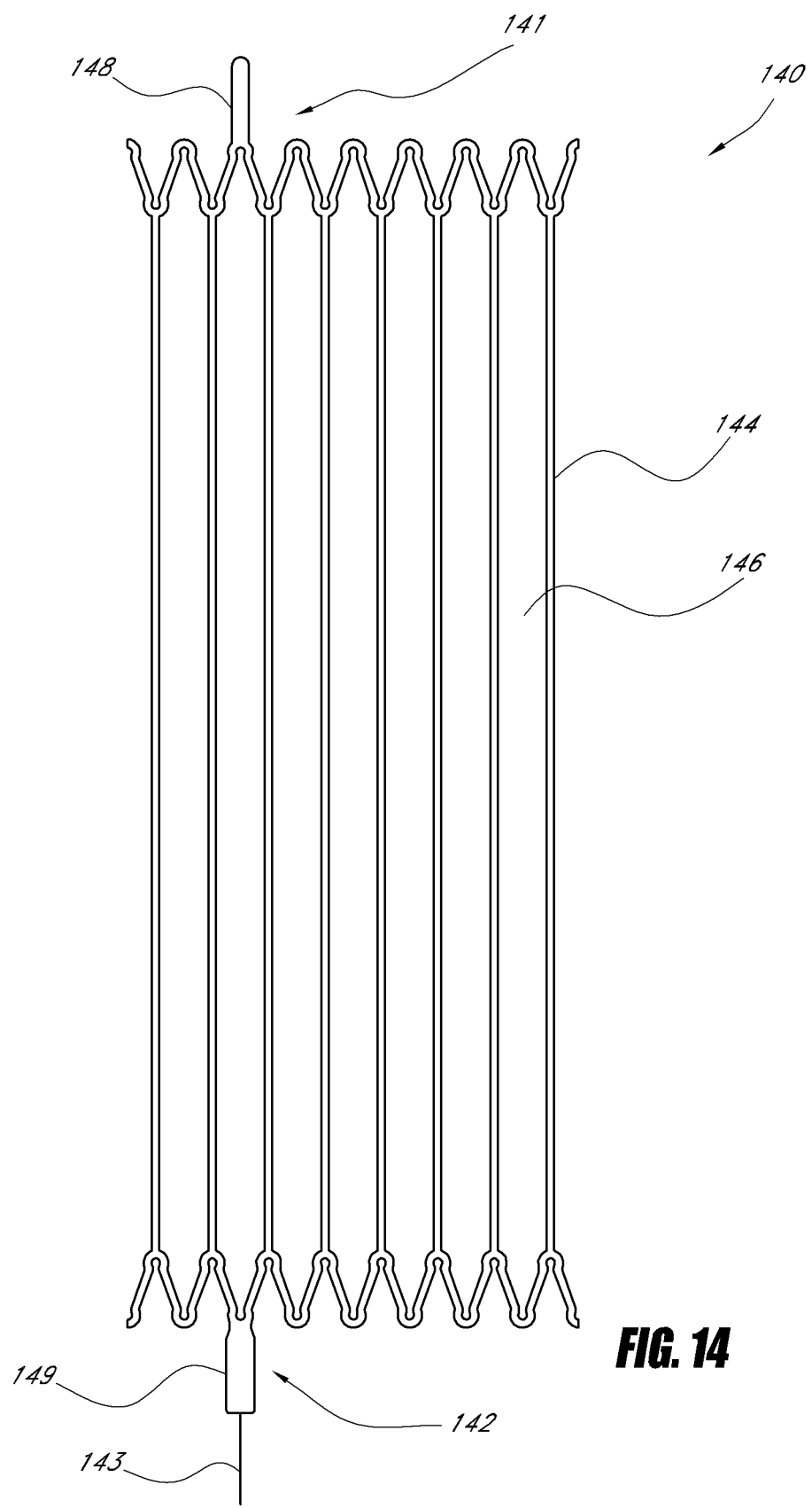
FIG. 14 illustrates an example embodiment of a generally spherical vascular remodeling device at a stage of an example manufacturing process.

FIG. 14 illustrates an example embodiment of a generally spherical vascular remodeling device 140 (e.g., having a football shape similar to the device 80) at a stage of an example manufacturing process comprising cutting and shaping a metallic tube (e.g., a laser cut hypotube). In some embodiments, the starting tube has a diameter between about 0.5 mm and about 3 mm or between about 1 mm and about 2 mm (e.g., about 1 mm, about 1.5 mm, about 2 mm, etc.). Other diameters are also possible. The device has a first or distal end 141 and a second or proximal end 142 substantially opposite the first end 141. A laser may cut out portions 146 of the tube, leaving a plurality of filaments 144 extending between the first end 141 and the second end 142. In the embodiment illustrated in FIG. 14, the filaments 144 are coupled at the first end 141 and the second end 142 (e.g., due to being integrally formed with the metallic tube and not cut away from each other). In some embodiments, a lead or tail, which may be used for releasing and/or retracting the device 140 after deployment, as described herein, may be attached to the device 140 (e.g., by adhering, soldering, welding, etc.). In certain embodiments, a tail 143 may be integral with the device 140 by being defined by the cut tube.

In some embodiments, the device 140 further comprises a radiopaque marker 148 proximate to the first end 141 and/or a radiopaque marker 149 proximate to the second end 142. In certain embodiments, the radiopaque marker 148 may extend at least partially into the aneurysm 20 when the device 140 is positioned at the junction of a bifurcation. In some embodiments, the radiopaque markers 148, 149 may be integral with the device by being defined by the cut tube. The radiopaque markers 148, 149 may aid in positioning the device 140 at the junction of a bifurcation.

The cut tube can then be expanded into a generally spherical shape through shape setting using a heat treatment process. The shape setting process may include several steps comprising of successively increasing diameters of generally spherical shapes using appropriate tooling to stretch and confine the cut tube into a new shape while heat treating it. At the end of the each heat treatment step, the cut tube assumes the shape in which it was confined during the heat treatment process. This process is then repeated to form a slightly larger size and a shape closer to the end product. The final shape (e.g., a football shape similar to the device 80) and size may obtained by several such steps. Other devices described herein (e.g., the devices 50, 110, 130) may also be formed using cut a metallic tube that is reshaped after being cut, although it will be appreciated that the pattern of the initial cut may be different, such that details about possible materials, dimensions, porosities, deployment methods, possibly coverings, etc. are not provided.

The disclosures of U.S. Provisional Patent App. No. 61/082,579, filed Jul. 22, 2008, and U.S. patent application Ser. No. 12/506,945, filed Jul. 21, 2009, may be relevant to certain of the generally spherical vascular remodeling devices described herein, and the disclosure each of those applications is incorporated herein by reference in its entirety.

Certain devices described herein may be advantageously used to treat aneurysms having a neck ratio (a ratio of fundus width to neck width) greater than about 2 to 1 and/or a neck width greater than about 4 mm. In treatment of such aneurysms, embolization coils may be prone to herniating into parent vessels because the size and/or shape of the aneurysm is not conducive to maintaining the coils in their inserted locus. In certain such embodiments, embolization coils are inserted in the fundus of the aneurysm after positioning a generally spherical device so that the embolization coils do not have an opportunity to herniate. It will be appreciated that certain devices described herein may also be used to treat aneurysms having a neck ratio less than about 2 to 1 and/or a neck width less than about 4 mm. In certain such embodiments, embolization coils are inserted in the fundus of the aneurysm before positioning a generally spherical device.

Certain devices described herein may advantageously be a single generally spherical device placed at a junction of a bifurcation rather than a plurality of tubular bifurcations. Certain such devices can span a neck of an aneurysm as well as arterial ostia. Positioning such devices may be less complicated, thereby reducing risks associated with, for example, than ensuring that a tubular device is properly anchored in an afferent vessel and in an efferent vessel.

Figure 1:
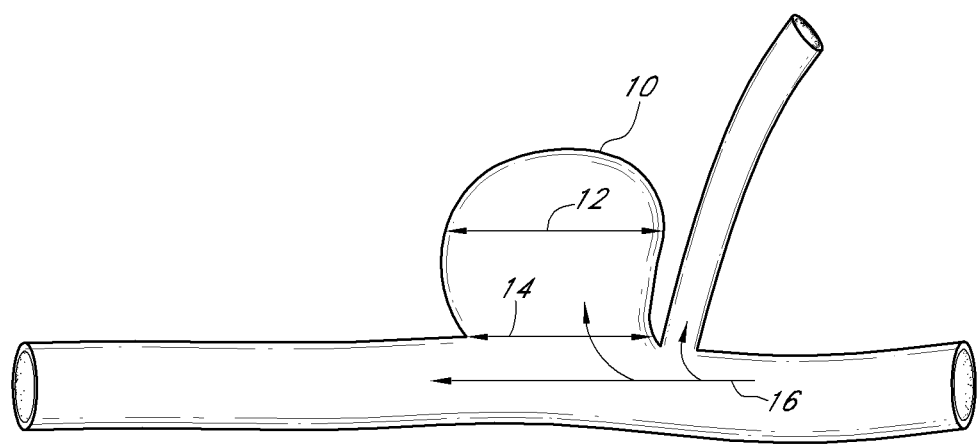
FIG. 1 illustrates an example embodiment of a side wall aneurysm.
Figure 2:
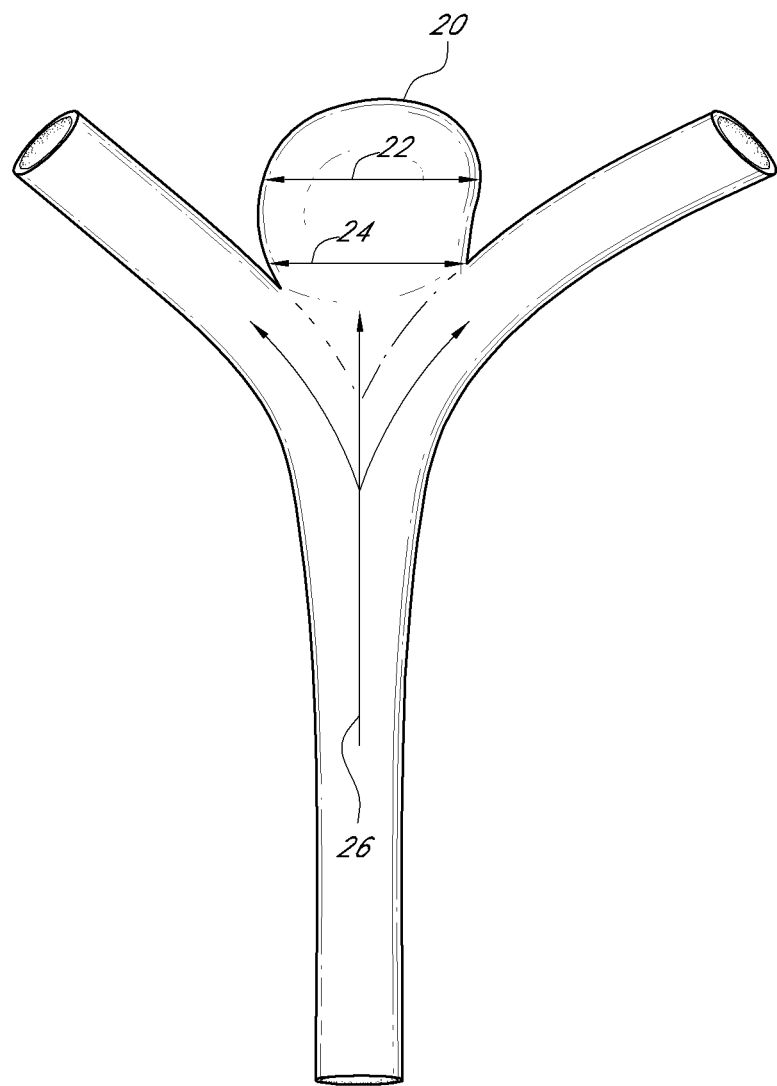
FIG. 2 illustrates an example embodiment of a bifurcation having an aneurysm.
Figure 3A:
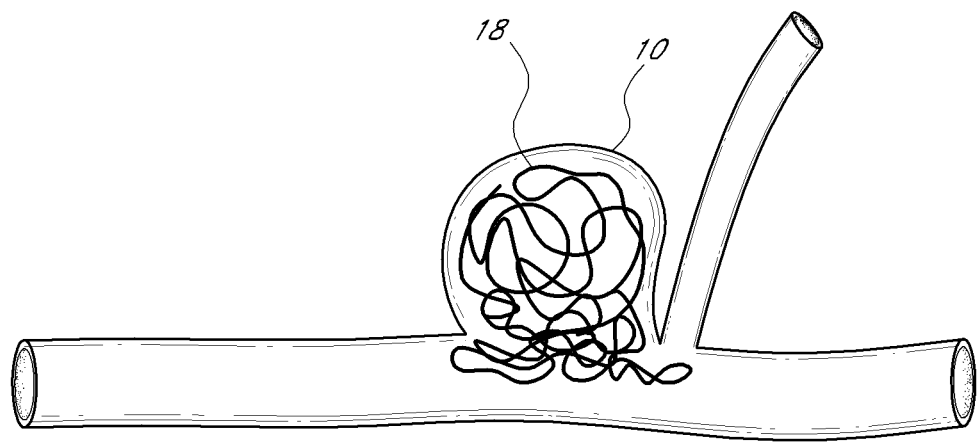
FIG. 3A illustrates an example embodiment of a side wall aneurysm with herniating embolization coils.
Figure 3B:
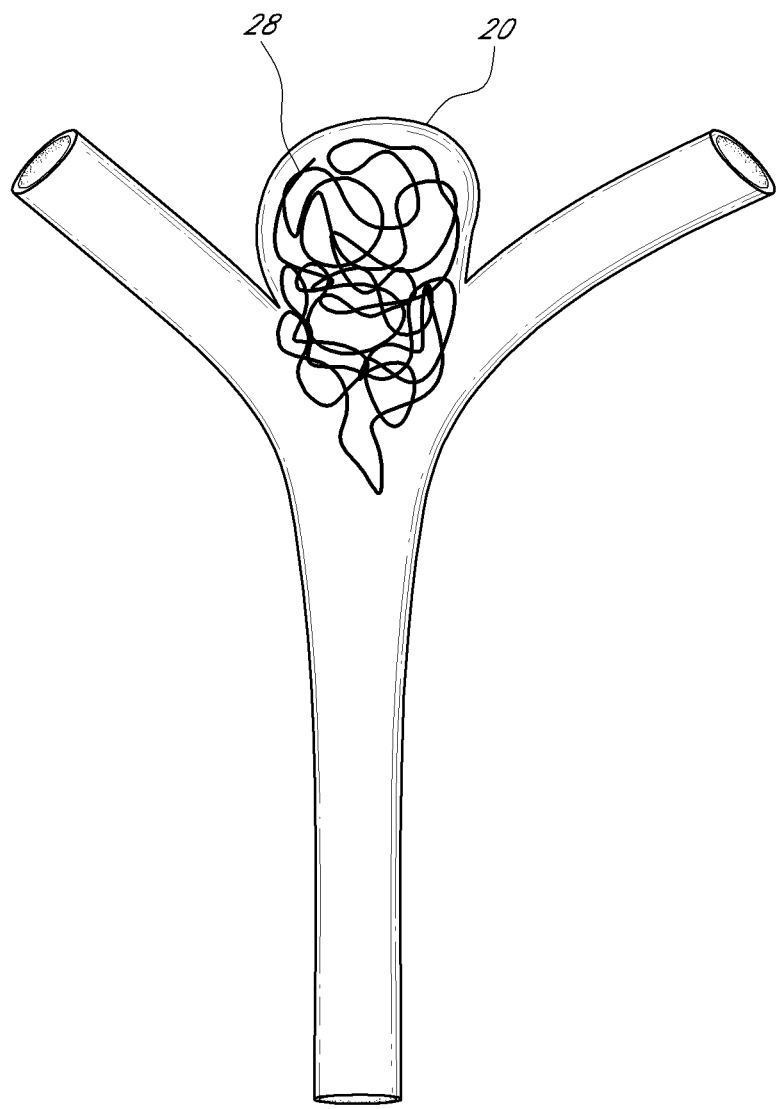
FIG. 3B illustrates an example embodiment of a bifurcation having an aneurysm with herniating embolization coils.
Figure 4A:
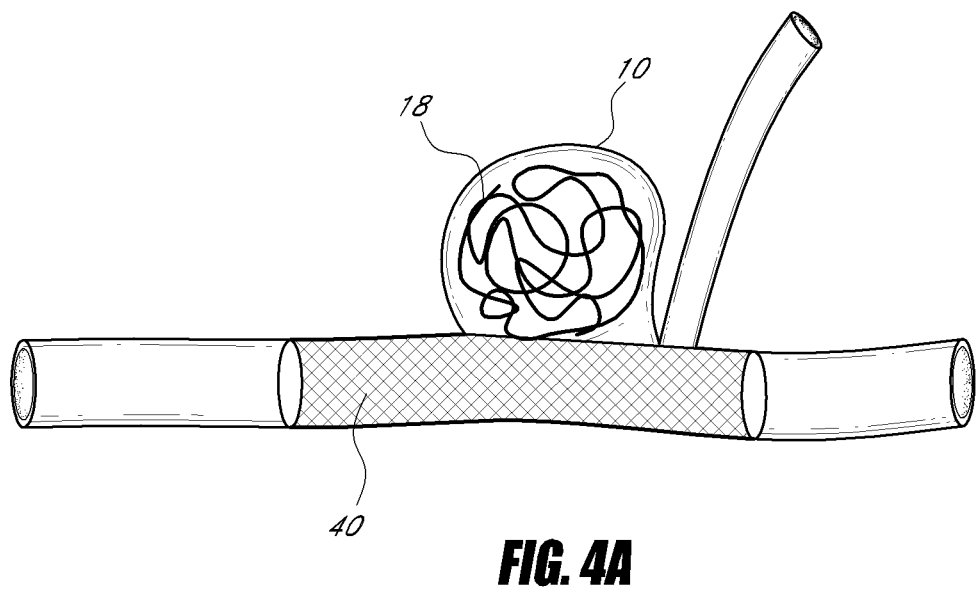
FIG. 4A illustrates an example embodiment of a side wall aneurysm treated with embolization coils and a tubular remodeling device.
Figure 4B:
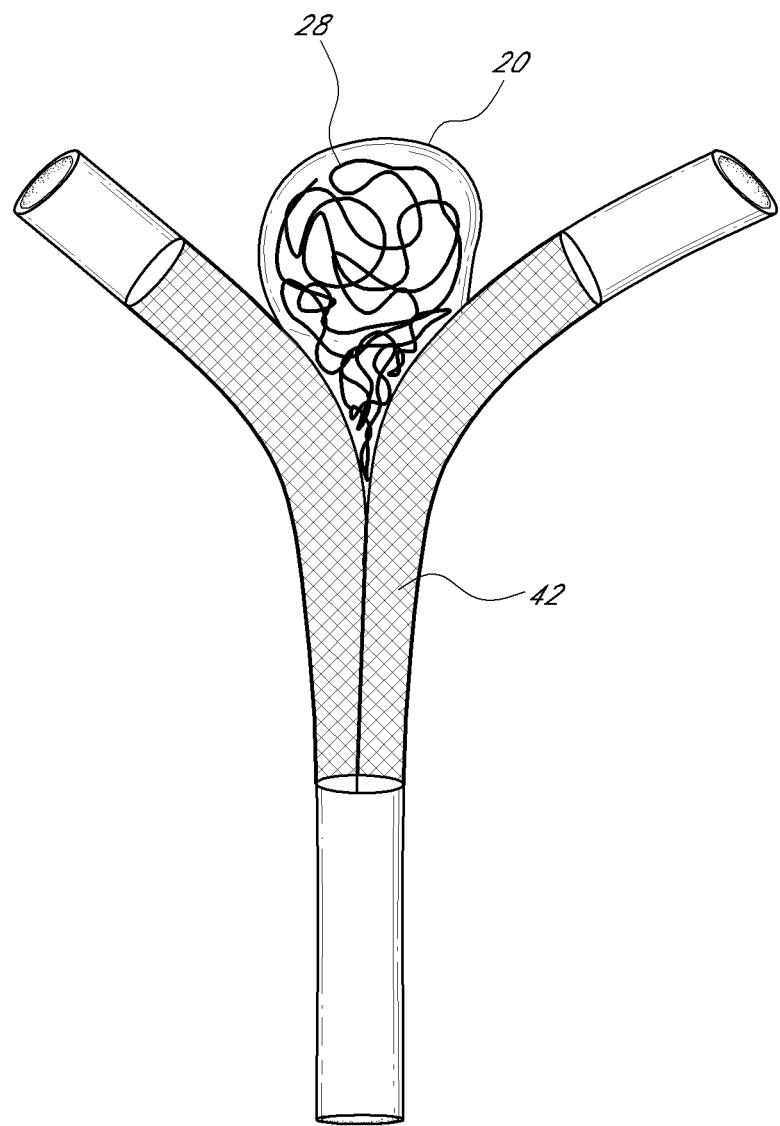
FIGS. 4B and 4C illustrates example embodiments of a bifurcation having an aneurysm treated with embolization coils and tubular remodeling devices.
Figure 4C:
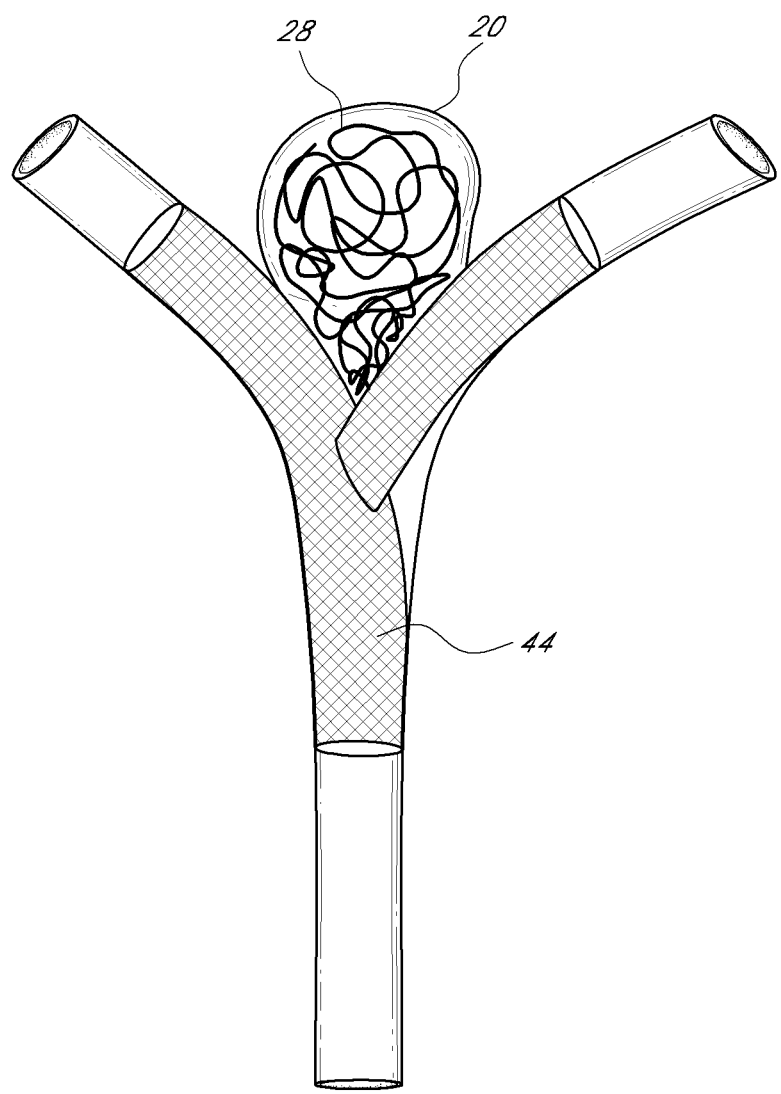

In some embodiments in which embolic material was previously inserted in an aneurysm but has herniated, certain devices described herein may be used as a "rescue device" to push the herniated material back into the aneurysm and to act as a scaffolding to inhibit or prevent further herniation or prolapse of the embolic material. In certain such embodiments, deployment of such devices may advantageously avoid traversal of the junction comprising the herniated material by wires or a catheter (e.g., there is no need to traverse wires or a catheter past the junction into an efferent vessel for positioning of the device as is generally needed to position tubular devices such as the devices 42, 44 illustrated in FIG. 4B and 4C), which may cause the herniated material to become tangled and/or dislodged and which may cause rupture of the aneurysm.

Although this invention has been disclosed in the context of certain embodiments and examples, it will be understood by those skilled in the art that the invention extends beyond the specifically disclosed embodiments to other alternative embodiments and/or uses of the invention and obvious modifications and equivalents thereof. In addition, while several variations of the embodiments of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. It should be understood that various features and aspects of the disclosed embodiments can be combined with, or substituted for, one another in order to form varying modes of the embodiments of the disclosed invention. Thus, it is intended that the scope of the invention herein disclosed should not be limited by the particular embodiments described above.

What is claimed is:

1. A method of treating an aneurysm at a junction of a bifurcation having an afferent vessel and efferent vessels, the aneurysm having a neck and a fundus, the method comprising:
   advancing a catheter proximate to the junction of the bifurcation, the catheter at least partially containing a generally spherical vascular remodeling device in a compressed state, wherein the device comprises a plurality of polymer filaments;
   positioning the device at the junction of the bifurcation; and
   withdrawing the catheter and leaving the device at the junction of the bifurcation, wherein a distal end of the device acts as a scaffolding to inhibit herniation of objects out of the neck of the aneurysm and wherein the device permits perfusion of fluid to the efferent vessels, and wherein proximal ends of the plurality of polymer filaments are coupled together by a bioabsorbable coupling at a proximal end of the device, wherein the coupling is configured to bioabsorb more quickly than does the plurality of polymer filaments, and wherein the proximal ends of the plurality of polymer filaments are configured to extend toward the afferent vessel after bioabsorption of the coupling.

2. The method of claim 1, wherein at least some of the polymer filaments comprise polyglycolic acid, polylactic acid, poly(lactic-co-glycolic acid), poly-epsilon-caprolactone, or naturally-derived bioabsorbable polymers.

3. The method of claim 1, wherein a first group of the polymer filaments comprise a first polymer having a first rate of bioabsorption and wherein a second group of the polymer filaments comprise a second polymer different than the first polymer, the second polymer having a second rate of bioabsorption different that the first rate of bioabsorption.

4. The method of claim 1, wherein the bifurcation is a neurovascular bifurcation.

5. The method of claim 1, wherein the device substantially conforms to a shape of the junction.

6. The method of claim 1, wherein positioning the device comprises: deploying the device from the catheter; and expanding the device.

7. The method of claim 6, wherein expanding the device comprises allowing the device to expand towards an uncompressed state.

8. The method of claim 6, wherein positioning the device further comprises, after expanding the device, releasing the device from the catheter.

9. The method of claim 8, wherein releasing the device comprises mechanically releasing or electrolytically releasing the device from the catheter.

10. The method of claim 8, further comprising: after expanding the device, retracting the device into the catheter; redeploying the device from the catheter; and re-expanding the device.

11. The method of claim 1, further comprising inserting embolic material in the fundus of the aneurysm, the objects comprising the embolic material.

* * * * *